(12) United States Patent
Farrell et al.

(10) Patent No.: US 7,458,947 B2
(45) Date of Patent: Dec. 2, 2008

(54) DYNAMIC SPLINT ASSEMBLIES

(75) Inventors: John Fletcher Farrell, Charlotte, NC (US); Henry B. Hoffman, Charlotte, NC (US); Ian D. Kovacevich, Charlotte, NC (US)

(73) Assignee: SAEBO, Inc., Charlotte, NC (US)

( * ) Notice: Subject to any disclaimer, the term of this patent is extended or adjusted under 35 U.S.C. 154(b) by 386 days.

(21) Appl. No.: 11/306,519

(22) Filed: Dec. 30, 2005

(65) Prior Publication Data

US 2007/0055191 A1 Mar. 8, 2007

Related U.S. Application Data

(60) Provisional application No. 60/640,370, filed on Dec. 30, 2004, provisional application No. 60/669,109, filed on Apr. 7, 2005.

(51) Int. Cl.
*A61F 5/00* (2006.01)
*A61F 13/00* (2006.01)

(52) U.S. Cl. .............. 602/21; 602/20; 602/22; 602/64

(58) Field of Classification Search .......... 602/5, 602/20–22, 60–64; 128/882, 888, 889, 877–879
See application file for complete search history.

(56) References Cited

U.S. PATENT DOCUMENTS

| 867,981 A | 10/1907 | Krizek |
|---|---|---|
| 3,769,970 A | 11/1973 | Swanson |
| 3,957,266 A | 5/1976 | Rice |
| 4,173,021 A | 10/1979 | Zuchner et al. |
| 4,602,620 A | 7/1986 | Marx |
| 4,765,320 A | 8/1988 | Lindemann et al. |
| 4,772,012 A | 9/1988 | Chesher |
| 4,790,301 A | 12/1988 | Silfverskiold |
| 4,858,903 A | 8/1989 | Tari |
| 4,865,285 A | 9/1989 | Gaggianese |
| 4,875,469 A | 10/1989 | Brook et al. |
| 4,881,275 A | 11/1989 | Cazares |
| 4,945,902 A | 8/1990 | Dorer et al. |
| 4,949,711 A | 8/1990 | Gyovai et al. |
| 4,960,114 A | 10/1990 | Dale |
| 4,977,890 A | 12/1990 | Mann |
| 5,056,504 A | 10/1991 | Mann |
| 5,162,030 A | 11/1992 | Tanski |
| 5,205,812 A | 4/1993 | Wasserman |
| 5,263,593 A | 11/1993 | Aida |

(Continued)

*Primary Examiner*—Kim M Lewis
(74) *Attorney, Agent, or Firm*—Tillman Wright, PLLC; Chad D. Tillman; James D. Wright

(57) ABSTRACT

A dynamic splint assembly for a hand includes a forearm support section configured to abut the dorsal side of a forearm and span a wrist; and a hand support section connected to the forearm support section. The hand support section is configured to abut the dorsal side of the hand including the dorsal side of the length of a finger. The hand support section comprises a resilient material that, in response to bending, such as during flexion of the finger, generates a continuous restoring force in opposition to such bending, whereby the finger in flexion is urged toward extension. The forearm support section, in contrast, does not generate, in response to bending, a continuous restoring force in opposition to such bending, whereby a wrist may be selectively oriented in one of many fixed dispositions having varying degrees of flexion and extension relative to a forearm.

19 Claims, 15 Drawing Sheets

U.S. PATENT DOCUMENTS

| | | |
|---|---|---|
| 5,295,948 A | 3/1994 | Gray |
| 5,415,623 A | 5/1995 | Cherubini |
| 5,415,624 A | 5/1995 | Williams |
| 5,453,064 A | 9/1995 | Williams, Jr. |
| 5,456,650 A | 10/1995 | Williams, Jr. et al. |
| 5,505,553 A | 4/1996 | Saviano et al. |
| 5,514,052 A | 5/1996 | Charles et al. |
| 5,538,488 A | 7/1996 | Villepigue |
| 5,542,667 A | 8/1996 | Lezdey et al. |
| 5,560,375 A | 10/1996 | Kabanek |
| 5,584,799 A | 12/1996 | Gray |
| 5,599,123 A | 2/1997 | Still |
| 5,637,078 A | 6/1997 | Varn |
| 5,697,103 A | 12/1997 | Wiggins |
| 5,807,293 A | 9/1998 | Wedge, Jr. |
| 5,820,577 A | 10/1998 | Taylor |
| 5,836,902 A | 11/1998 | Gray |
| 5,921,945 A | 7/1999 | Gray |
| 6,033,139 A | 3/2000 | Dutcher |
| 6,702,725 B2 | 3/2004 | Hoffman et al. |
| 6,854,913 B2 | 2/2005 | Farrell et al. |
| 7,001,352 B2 | 2/2006 | Farrell et al. |
| 2002/0077578 A1* | 6/2002 | Bonutti ................ 602/75 |
| 2002/0198089 A1 | 12/2002 | Hoffman et al. |
| 2003/0162634 A1 | 8/2003 | Farrell et al. |
| 2003/0195093 A1 | 10/2003 | White |
| 2003/0228185 A1 | 12/2003 | Farrell et al. |

* cited by examiner

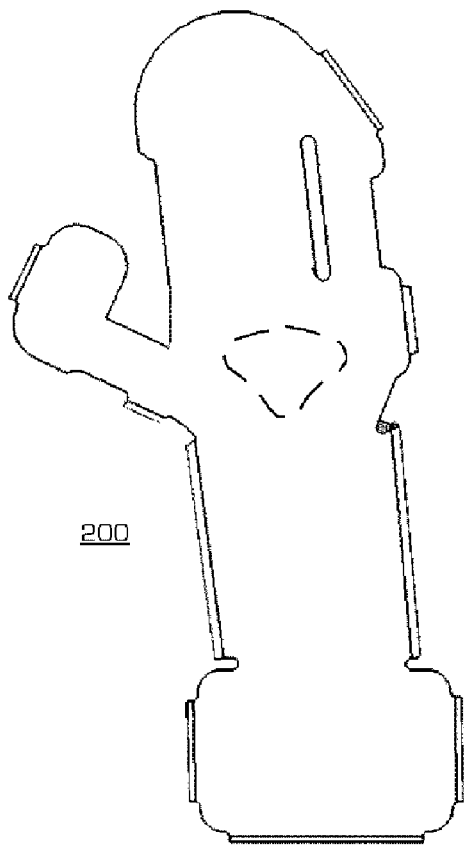
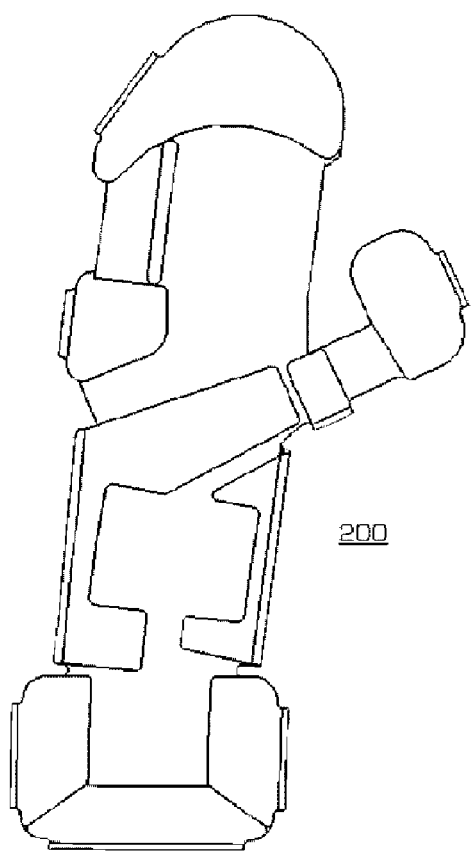
FIG. 16B
FIG. 16A
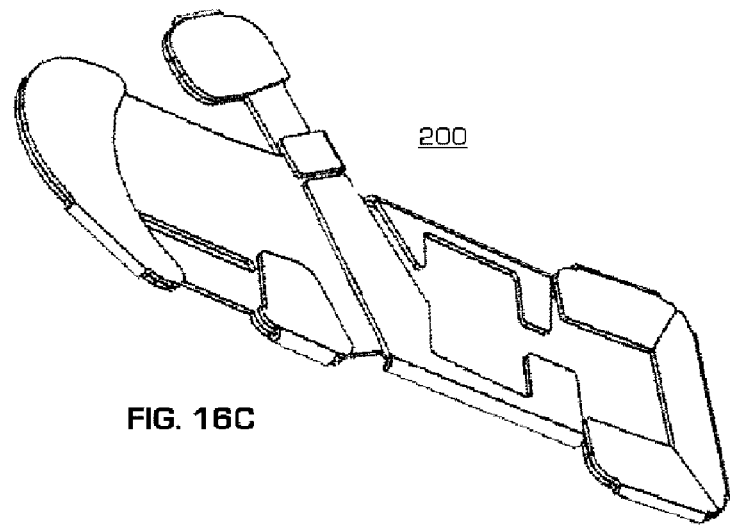
FIG. 16C

DYNAMIC SPLINT ASSEMBLIES

CROSS-REFERENCE TO RELATED APPLICATIONS

The present application for purposes of the United States is a nonprovisional patent application of, and claims priority under 35 U.S.C. § 119(e) to each of U.S. provisional patent application Ser. No. 60/640,370, filed on Dec. 30, 2004, and titled "Dynamic Splint Assembly," which provisional patent application is incorporated by reference herein; and to U.S. provisional patent application Ser. No. 60/669,109, filed on Apr. 7, 2005, and titled "Dynamic Splint Assembly," which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

FIELD OF THE INVENTION

The invention generally relates to orthoses and, in particular, to dynamic splint assemblies for the hand.

BACKGROUND OF THE INVENTION

Many people suffering a neurological injury from stroke, cerebral palsy, brain injury, etc., have upper extremity impairments. Many have some shoulder and elbow movements, but have a non-functioning hand and are unable to extend their wrist or fingers to grasp an object. This is usually due to hypertonicity, described in U.S. Pat. No. 5,807,293 as a condition where the flexor or extensor muscles in the upper extremities are spastic and resist positioning. Dynamic splints can be used to offer slight resistance to hold joints in certain positions. An effective dynamic splint designed to be used for hypertonicity must offer enough force to balance the effects of the increased muscle tone. Such a dynamic splint for the hand is disclosed and described, for example, in United States Patent Application Publication No. US2003/0162634 to Farrell et al. Embodiments of the invention present yet additional, alternative designs for dynamic splint assemblies for a hand.

SUMMARY OF THE INVENTION

The invention includes many aspects and features.

In a first aspect of the invention, a dynamic splint assembly for a hand includes a forearm support section configured to abut the volar side of a forearm and span a wrist and a hand support section connected to and extending from an end of the forearm support section. The hand support section is configured to abut the volar side of the hand including at least the volar side of the length of one finger. The hand support section comprises a resilient material that, in response to bending, such as during flexion of an abutted finger, generates a continuous restoring force in opposition to such bending, whereby an abutted finger in flexion is urged toward extension. The forearm support section comprises a malleable material that does not generate, in response to bending, a continuous restoring force in opposition to such bending, whereby a wrist may be selectively oriented in one of a plurality of fixed dispositions having varying degrees of flexion and extension relative to a forearm when the dynamic splint assembly is donned.

In a feature of this aspect, the hand support section is releasably connected to the forearm support section. For instance, the hand support section may be releasably connected to the forearm support section such that the hand support section may be readily substituted with another hand support section comprising a material having a different resiliency. In an alternative feature, the hand support section is permanently connected to the forearm support section.

In additional features, the resilient material of the hand support section comprises a thin sheet of spring steel or a resilient plastic and the forearm support section comprises a thin sheet of semirigid but malleable steel or plastic. Alternatively, the hand support section and the forearm support section are integrally formed and constitute a single piece.

In another feature, the forearm support section comprises protuberances on opposite ulnar and radial sides thereof proximal an end of the forearm support section, whereby each protuberance may be bent at a selective angle relative to the forearm support section for stabilization of the proximal end of the forearm support section on the forearm.

In still another feature, the forearm support section further comprises a thumb support section configured to abut the volar side of the length of the thumb of the hand. In this feature, the thumb support section may comprise a malleable material that does not generate a continuous restoring force in opposition to bending, whereby a thumb may be selectively oriented in one of a plurality of fixed dispositions having varying degrees of opposition, abduction, adduction, flexion, and extension of the thumb when the dynamic splint assembly is donned. Alternatively, the thumb support section may comprises a resilient material that, in response to bending, such as during flexion of an abutted thumb, generates a continuous restoring force in opposition to such bending, whereby an abutted thumb in flexion is urged toward extension. In either scenario, the thumb support section also may further include a thumb restraint section that protrudes from a distal end of the thumb support section and that is configured to block flexion and adductional movement of the thumb relative to the thumb support section.

In yet another feature, the dynamic splint assembly includes a plurality of straps for securing the connected forearm support section to the forearm and the hand support section to a hand. With respect to this feature, the hand support section may define a slot having an extent sufficient for two or three of the straps to concurrently extend therethrough, with the slot preferably extending proximate the radial side of a little finger and the ulnar side of a ring finger when the dynamic splint assembly is donned.

One of the plurality of straps also may include or be comprised of a non-slip material on a volar side thereof for frictional engagement with the skin of the hand. The non-slip material preferably is a silicone-based composite material that does not include latex, and may be in the form of raised areas in the shape of, for example, chevrons. The hand support section also may define: a side indentation along an ulnar side thereof for receipt and retention therein of one of the straps when wrapped around the ulnar side of the hand support section, the strap configured for wrapping around the little finger of the hand; and/or a side indentation along a radial side thereof for receipt and retention therein of one of the straps when wrapped around the radial side of the hand support section, the strap configured for wrapping around the index long and ring fingers of the hand. Similarly, the forearm support section may further include a thumb support section configured to abut the volar side of the length of the thumb of the hand, wherein the thumb support section defines side indentations along opposite sides thereof for receipt and retention therein of one of the straps when wrapped around the ulnar and radial sides of the thumb support section, the strap configured for wrapping around the thumb of the hand. The combined hand support section and the forearm support section also may define a side indentation along an ulnar side thereof for receipt and retention therein of one of the straps when wrapped around the ulnar side of the hand support section, the strap configured for wrapping around the palmer portion and the dorsum of the hand.

In another aspect of the invention, a dynamic splint assembly for a hand includes: a forearm support section configured to abut the volar side of a forearm and span a wrist; and a hand support section connected to and extending from an end of the forearm support section, the hand support section configured to abut the volar side of the hand including at least the volar side of the length of one finger. The forearm support section comprises a malleable material that does not generate, in response to bending, a continuous restoring force in opposition to such bending, whereby a wrist may be selectively oriented in one of a plurality of fixed dispositions having varying degrees of flexion and extension relative to a forearm when the dynamic splint assembly is donned. The forearm support section further comprises a thumb support section configured to abut the volar side of the length of the thumb, the thumb support section comprising a resilient material that, in response to bending, such as during flexion of an abutted thumb, generates a continuous restoring force in opposition to such bending, whereby an abutted thumb in flexion is urged toward extension.

In a feature of this aspect, the hand support section comprises a resilient material that, in response to bending, such as during flexion of an abutted finger, generates a continuous restoring force in opposition to such bending, whereby an abutted finger in flexion is urged toward extension, and the thumb support section comprises a thumb restraint section that protrudes from a distal end of the thumb support section, the thumb restraint section configured to block flexion and adductional movement of the thumb relative to the thumb support section, the thumb restraint section comprising a malleable material that does not generate, in response to bending, a continuous restoring force in opposition to such bending.

In another feature, the hand support section comprises a malleable material that does not generate, in response to bending, a continuous restoring force in opposition to such bending, whereby the fingers may be selectively oriented in one of a plurality of fixed dispositions having varying degrees of flexion and extension relative to the palm of the hand when the dynamic splint assembly is donned. The thumb support section also may include a thumb restraint section that protrudes from a distal end of the thumb support section, the thumb restraint section configured to block flexion and adductional movement of the thumb relative to the thumb support section.

In still yet another aspect of the invention, a method for donning a dynamic splint assembly for a hand includes the steps of bending a forearm support section such that a wrist is oriented in a selected one of a plurality of fixed dispositions having varying degrees of flexion and extension relative to a forearm when the dynamic splint assembly is donned; positioning the forearm support section such that the forearm support section abuts the volar side of a forearm and such that the forearm support section spans the wrist with the wrist oriented in the selected fixed disposition of flexion and extension relative to the forearm support section; positioning a hand support section such that the hand support section abuts the volar side of the hand including at least the volar side of the length of a finger and such that the hand support section generates a continuous restoring force during flexion of the abutted finger whereby the abutted finger in flexion is urged toward extension; and securing the forearm support section and the hand support section on the forearm and hand with one or more straps.

In a feature of this aspect, the hand support section extends below and abuts the volar surface of each of the fingers.

In another feature, the hand support section permits the finger to move through flexion and urging the finger back into extension via a low load long duration stretch.

In another feature, the step of securing the forearm support section on the forearm with a strap comprises extending a strap around the ulnar side of the forearm support section, over the forearm, and around the radial side of the forearm support section. In this feature, the strap may further extend over stabilizers disposed on proximal and on each of the ulnar and radial sides of the forearm support section.

In another feature, the step of securing the hand support section on the hand with straps comprises positioning a strap to extend through the slot formed in the hand support section that extends proximate the radial side of the little finger and proximate the ulnar side of the ring finger, then over the little finger and around the ulnar side of the hand support section. In this feature, the strap extends around the ulnar side of the hand support section further is received and retained within a side indentation of the ulnar side of the hand support section proximate the ulnar side of the little finger.

In another feature the step of securing the hand support section on the hand with straps comprises extending a strap passing through a slot formed in the hand support section that extends proximate the radial side of the little finger and proximate the ulnar side of the ring finger, over the ring, middle, and index fingers, around the radial side of the hand support section. In this feature, the strap extending around the radial side of the hand support section further may be received and retained within a side indentation of the radial side of the hand support section proximate the radial side of the index finger; the step of securing the hand support section on the hand with straps may include passing a strap through the slot formed in the hand support section, over the little finger, and around the ulnar side of the hand support section, whereby at least two straps extend through the slot; and the strap extending around the radial side of the hand support section may abut the proximal phalanx of each of the ring, middle, and index fingers proximate the PIP joints thereof.

Still yet, the step of securing the hand support section on the hand with straps may further include passing an additional strap through the slot formed in the hand support section, over the ring, middle, and index fingers, around the radial side of the hand support section, whereby at least two straps extend through the slot, wherein the additional strap passing through the slot and around the radial side of the hand support section abuts the middle phalanx of each of the ring, middle, and index fingers, wherein the additional strap extending around the radial side of the hand support section further is received and retained within the side indentation of the radial side of the hand support section, and/or wherein the step of securing the hand support section on the hand with straps comprises extending a strap passing through the slot formed in the hand support section, whereby at least three straps extend through the slot. Two around the ring, middle, and index fingers and one over the little finger.

In another feature, the step of securing the hand support section on the hand with straps comprises extending a strap around the radial side of the hand support section, over the dorsum of the hand, and around an ulnar side of the hand support section. In this feature the strap extending around the ulnar side of the hand support section further may be received and retained within a side indentation defined by the ulnar side of the hand support section and the ulnar side of the forearm support section proximate the connection between the hand support section and the forearm support section.

In another feature, the forearm support section comprises a thumb support section configured to abut the volar side of the thumb of the hand, and wherein the step of securing the forearm support section on the forearm with a strap comprises extending a strap around the ulnar side of the thumb support section, over the thumb, and around the radial side of the thumb support section. In this feature, the strap extends over the proximal phalanx near the IP joint of the thumb, and the strap may be received and retained within a side indentation located on the ulnar side of the thumb support section and within a side indentation located on the radial side of the thumb support section. Flexion and adductional movement of the thumb relative to the thumb support section also may be restrained by bending a thumb restraint section that protrudes from a distal end of the thumb support section into blocking disposition of the thumb.

In another aspect of the invention, a dynamic splint assembly for a hand includes: a forearm support section configured to abut the volar side of a forearm and span a wrist, the forearm support section comprising a malleable material that does not generate, in response to bending, a continuous restoring force in opposition to such bending; a hand support section connected to and extending from an end of the forearm support section, the hand support section configured to abut the volar side of the hand including at least the volar side of the length of one finger, the hand support section comprising a resilient material that, in response to bending, such as during flexion of an abutted finger, generates a continuous restoring force in opposition to such bending, whereby an abutted finger in flexion is urged toward extension; a top liner including an area of hook-and-loop material on a dorsal side thereof; a bottom liner including an area of hook-and-loop material on a volar side thereof; and a covering comprising a pliable padded material, the covering serving as the exterior dorsal surface of the dynamic splint assembly and including, on a volar surface thereof, an area of hook-and-loop material that is capable of interlocking engagement with the areas of hook-and-loop material of the top and bottom liners. Furthermore, the volar surface of the top liner is attached to the dorsal surface of the connected hand and forearm support sections; a dorsal surface of the bottom liner is attached to the volar surface of the connected hand and forearm support sections; and the volar surface of the covering is releasably attached via hook-and-loop engagement to the dorsal surface of the top liner in covering disposition of the connected hand and forearm support sections, extends around the sides of the hand and forearm support sections, and is further releasably attached via hook-and-loop engagement to the volar side of the bottom liner.

In a feature of this aspect, the material of the covering allows air and moisture to circulate and wick away from the hand.

In a feature of this aspect, the dynamic splint assembly further includes a pad extending between the hand support section and the covering and configured for cushioning support of the palmer arch. The pad may be disposed within an area of the top liner that corresponds to the area of the palmer arch.

In other features, the dynamic splint assembly further includes a pad extending between the hand support section and the covering and configured for cushioning support of the fingers, and the dynamic splint assembly further includes a pad extending between the hand support section and the covering configured for cushioning support of the thumb.

In a feature of this aspect, each of the top and bottom liners includes a profile that corresponds to and registers with the profile of the forearm support section combined with the hand support section.

In a feature of this aspect, the area of hook-and-loop material on the top liner substantially corresponds to the entire dorsal surface of the top liner.

In a feature of this aspect, the area of hook-and-loop material on the bottom liner substantially corresponds to the entire volar surface of the bottom liner.

In a feature of this aspect, the covering, top liner, hand support section, and bottom liner top each defines an opening, the openings registering with one another to define a slot of the dynamic splint assembly for receipt there through of a strap.

In still yet another feature of this aspect, the covering comprises a non-slip material that is adhered, screened, printed, or otherwise affixed in areas of the dorsal surface of the covering for increased frictional abutment with the fingers, and thumb of the hand. The non-slip material preferably is a silicone-based composite material that does not include latex, and may be in the form of raised areas in the shape of, for example, chevrons.

In yet another aspect of the invention, a splint assembly for a hand includes a forearm support section configured to abut the volar side of a forearm and span a wrist; a hand support section connected to and extending from an end of the forearm support section, the hand support section configured to abut the volar side of the hand including at least the volar side of the length of one finger; and at least one strap securing the hand section to the hand, the strap including a surface comprising a non-slip material and configured to abut and contact the skin of the thumb, finger, or dorsum of the hand.

In a feature of this aspect, the splint assembly may be a static splint assembly having no dynamic sections. In an alternative feature, the splint assembly comprises a dynamic splint assembly having at least one dynamic support section. The dynamic support section may be the hand support section. In this respect, the hand support section comprises a resilient material that, in response to bending, such as during flexion of an abutted finger, generates a continuous restoring force in opposition to such bending, whereby an abutted finger in flexion is urged toward extension. The forearm support section may comprise a malleable material that does not generate, in response to bending, a continuous restoring force in opposition to such bending, whereby a wrist may be selectively oriented in one of a plurality of fixed dispositions having varying degrees of flexion and extension relative to a forearm when the dynamic splint assembly is donned.

In another feature of this aspect, the hand support section defines a slot through which at least one strap extends, the slot being configured to extend proximate the length of the radial side of the little finger and proximate the length of the ulnar side of the ring finger. The strap may be configured to cover the little finger and to extend around the ulnar side of the hand support section, and the hand support section may define a side indentation proximate the ulnar side of the little finger within which the strap is received and retained.

Alternatively, the strap may be configured to cover the ring, middle, and index finger and to extend around the radial side of the hand support section, and the hand support section may define a side indentation proximate the radial side of the index finger within which the strap is received and retained. In this case, an additional strap may extend through the slot and be configured to cover the little finger and to extend around the ulnar side of the hand support section, with the hand support section defining a side indentation proximate the ulnar side of the little finger within which the strap is received and retained, whereby the little finger is separately secured by a strap and the index, middle, and ring fingers are collectively secured by a strap. A third strap also may extend through the slot and be configured to cover the index, middle, and ring fingers (and preferably would be configured to abut the middle phalanx of each of the index, middle, and ring fingers).

In another aspect of the invention, a strap for securing a splint assembly for a hand includes a surface having a non-slip material and configured to abut and contact the skin of the thumb, finger, or dorsum of the hand.

In still another aspect of the invention, a splint assembly for a hand includes: a forearm support section configured to abut the volar side of a forearm and span a wrist; a hand support section connected to and extending from an end of the forearm support section, the hand support section configured to abut the volar side of the hand including at least the volar side of the length of one finger; a first strap for securing the hand support section to a hand, the first strap positioned to extend through a slot defined by the hand support section, the slot being configured to extend proximate the length of the radial side of the little finger and proximate the length of the ulnar side of the ring finger, the first strap configured to extend over the little finger and around an ulnar side of the hand support section; and a second strap for securing the hand support section to a hand, the second strap positioned to extend concurrently with the first strap through the slot defined by the hand support section, the second strap configured to extend over the ring, middle, and index fingers and around a radial side of the hand support section.

In a feature, the splint assembly further includes a third strap for securing the hand support section to a hand, the second strap positioned to extend concurrently with the first and second strap through the slot defined by the hand support section, the second strap configured to extend over the ring, middle, and index fingers and around a radial side of the hand support section. The hand support section also defines a side indentation on the ulnar side thereof within which the first strap is received and retained, and the hand support section defines a side indentation on the radial side thereof within which the second strap is received and retained.

Another aspect of the invention simply comprises a splint assembly for hand. The splint assembly may be a dynamic splint assembly or may a static splint assembly.

In addition to the aforementioned aspects and features of the invention, it should be noted that the invention further includes the various possible combinations of such aspects and features.

BRIEF DESCRIPTION OF THE DRAWINGS

One or more preferred embodiments of the invention now will be described in detail with reference to the accompanying drawings, which are for the purpose only of illustrating dynamic splint assemblies and components thereof and are not intended to be to scale:

FIG. 16A is a top plan view of the dynamic splint assembly of FIG. 10 in an assembled configuration.

FIG. 16B is a bottom plan view of the dynamic splint assembly of FIG. 10 in an assembled configuration.

FIG. 16C is a perspective view of the bottom of the dynamic splint assembly of FIG. 10 in an assembled configuration.

DETAILED DESCRIPTION OF THE INVENTION

Figure 1:
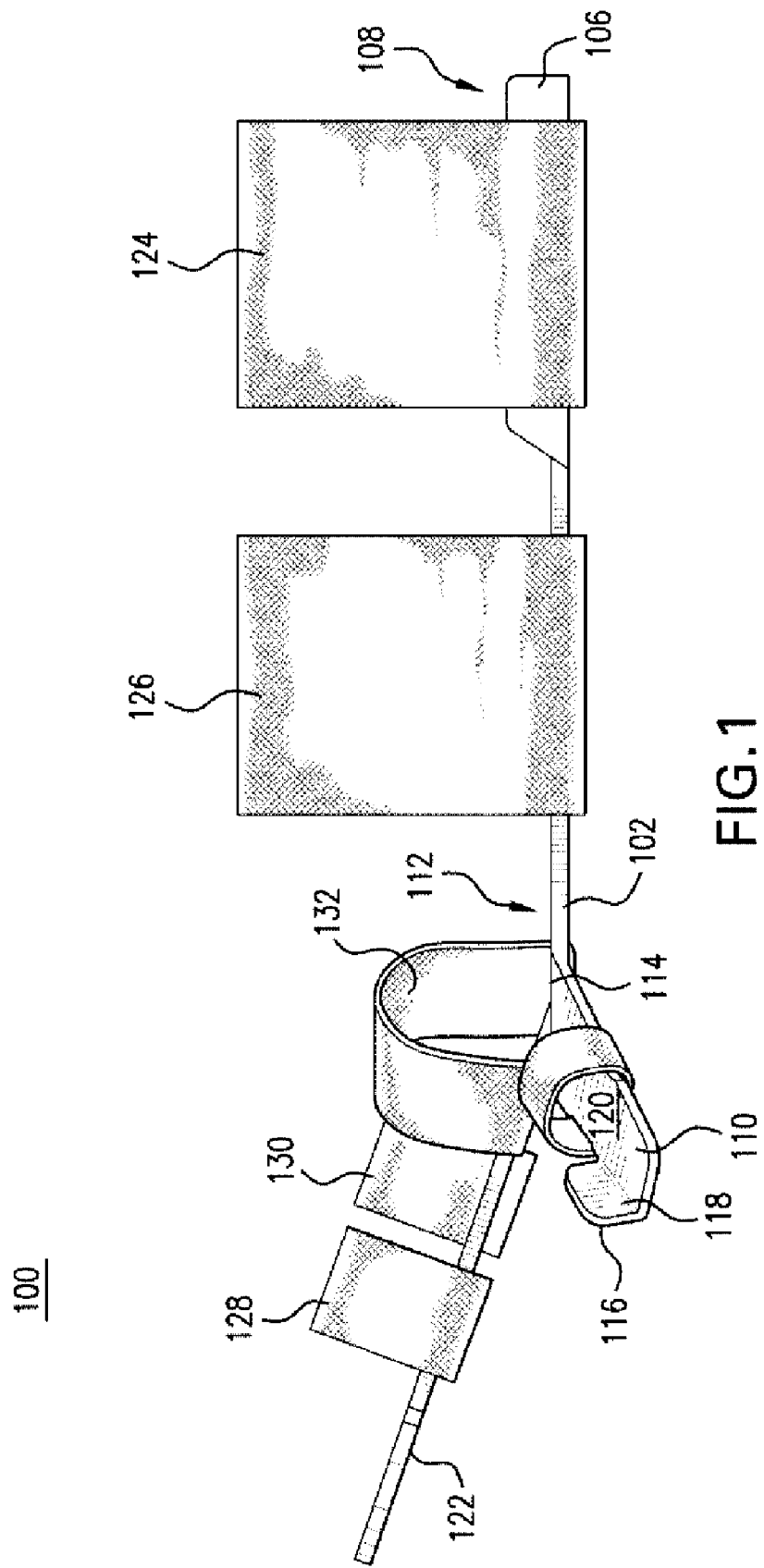
FIG. 1 is an elevational view of a left side of a dynamic splint assembly for a right hand in accordance with an embodiment of the invention.
Figure 2:
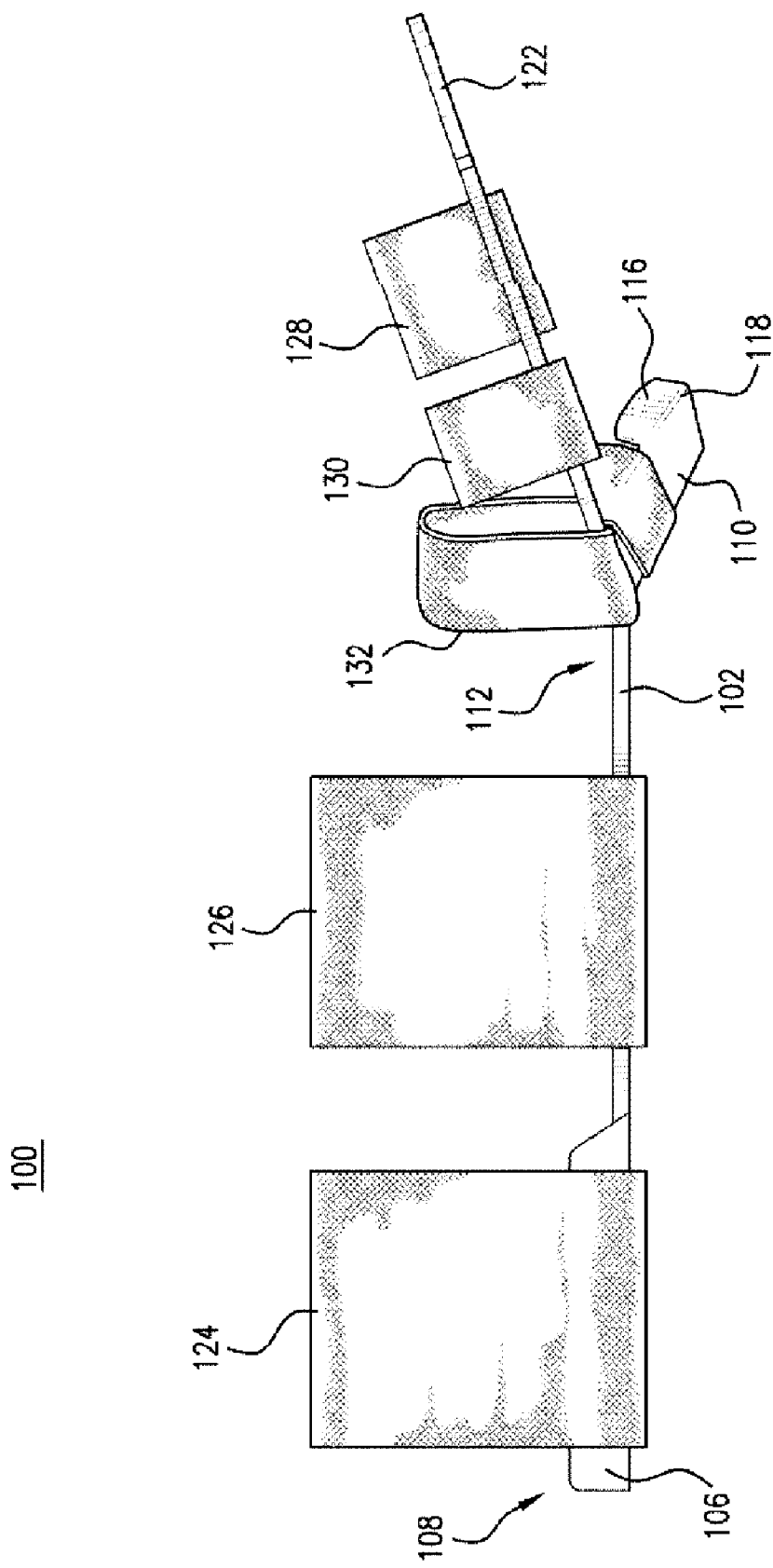
FIG. 2 is an elevational view of a right side of the dynamic splint assembly of FIG. 1.
Figure 3:
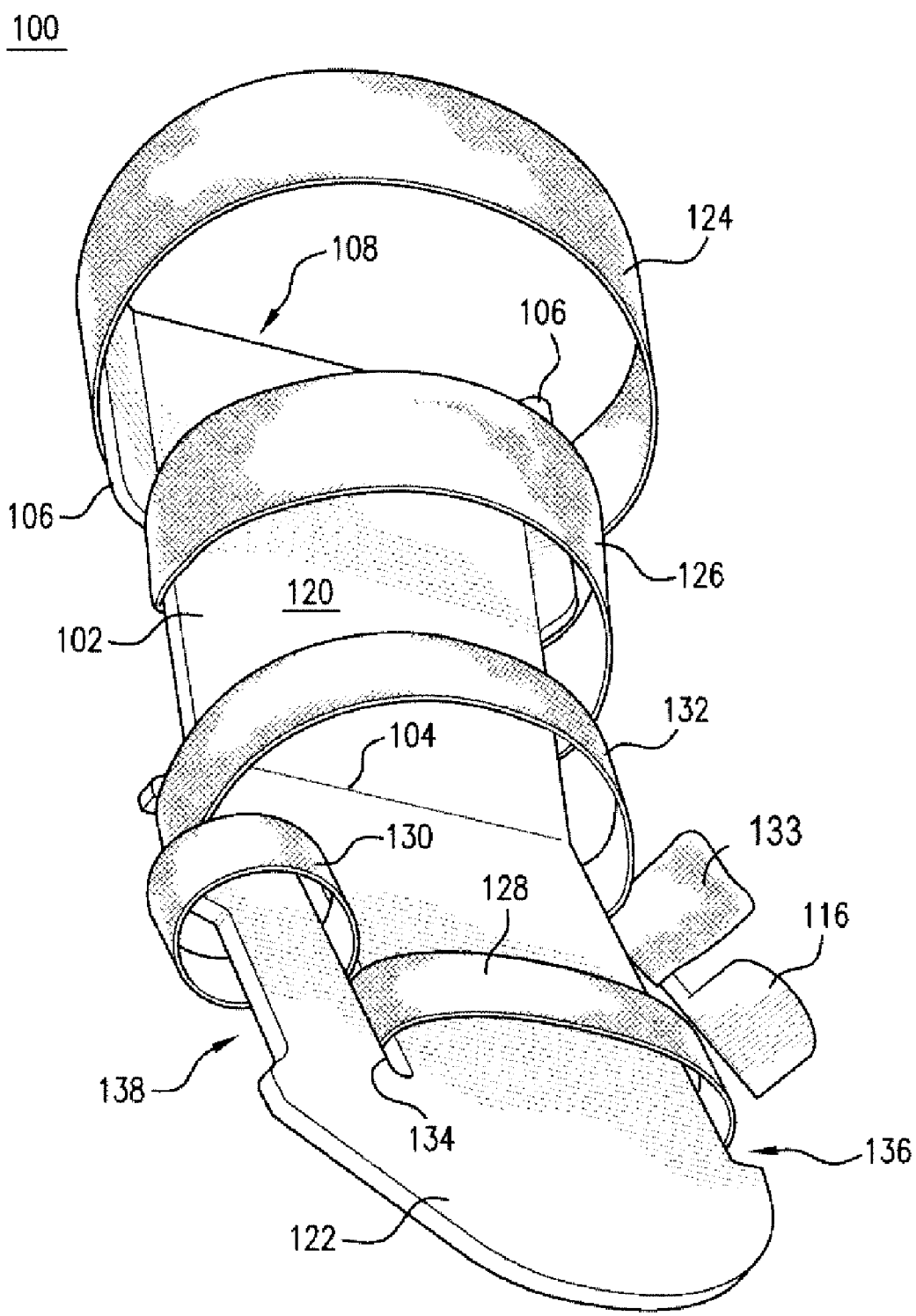
FIG. 3 is a top perspective view of a front of the dynamic splint assembly of FIG. 1.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Moreover, many embodiments, such as adaptations, variations, modifications, and equivalent arrangements, will be implicitly disclosed by the embodiments described herein and fall within the scope of the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, several terms such as "dorsal," "volar," "radial," and "ulnar" are used herein with reference to features of the human hand. Indeed, descriptions herein of one or more illustrated embodiments of the invention sometimes are made with such terms that may imply that the embodiment is disposed on a forearm and hand. Use of such terms of reference is made herein in order to facilitate an understanding of the invention, and the forearm and the hand are not considered in such embodiments to be actual elements of the invention.

Moreover, for the purpose of interpreting these terms of reference, the reader should consider a forearm and open hand resting palm-side down upon a planar desktop, with the forearm and palm generally contacting the desktop, and with the fingers and thumb generally straight and resting their lengths on the desktop. The volar sides of the forearm, wrist, hand, and fingers are generally disposed toward and contact the desktop. Thus, the fingerprints generally are found on the volar sides of fingertips. The dorsal sides of the forearm, wrist, hand, and fingers generally face in opposite direction to the volar sides of the forearm, wrist, hand, and fingers. These dorsal sides thus would be generally oriented away from the desktop. For example, fingernails generally grow from the dorsal sides of the fingers. The side of the hand from which the thumb depends defines the radial side of the forearm, wrist, and hand. In contrast, the side of the hand opposing the radial side defines the ulnar side of the forearm, wrist, and hand. For example, the fourth finger from the thumb of the hand, generally the smallest finger often called the "pinkie" finger, depends from the ulnar side of the hand. In view of these clarifications, these terms of reference are unambiguous and are well-defined with regard to essentially any hand or wrist, including both the left hand and right hand.

Regarding the views of the figures, dorsal views herein refer to views directed toward dorsal sides. For example, a dorsal view of a hand shows the dorsal side of the hand, which side is sometimes called the back of the hand. Similarly, a radial view of a hand generally would include a showing of the thumb, a volar view of a hand generally would include a showing of the palm, and an ulnar view of a hand generally would include a showing of the fourth finger from the thumb.

Regarding planes and axes, volar-dorsal planes are generally perpendicular to radial-ulnar planes, and the forearm generally defines a longitudinal axis. The reader should consider again the forearm and hand resting palm-side down on a planar desktop, particularly when the hand and forearm are comfortably aligned and the fingers are extended straight and held tightly together. In this disposition of the forearm and hand, the plane of the desktop defines a radial-ulnar plane; a longitudinal axis is defined along the length of the forearm; and the four fingers of the hand extend generally parallel to the longitudinal axis. Furthermore, rotation of a radial-ulnar plane by ninety degrees about the longitudinal axis produces a volar-dorsal plane. For example, when a postcard is slipped between adjacent fingers such that an edge of the postcard abuts the desktop and is held parallel to the longitudinal axis, and such that the postcard stands vertically and ninety degrees from the plane of the desktop, the postcard defines a volar-dorsal plane.

Furthermore, terms of reference such as "phalanx," "phalange," and "interphalangeal joint," which terms are well-known and are found in the prior art, may be used herein with reference to the skeletal anatomy of the human hand. Indeed, descriptions herein of one or more illustrated embodiments of the invention sometimes are made with such terms that may imply that the embodiment is disposed on or abuts the hand. Use of such terms of reference is made herein in order to facilitate an understanding of the invention while the hand and portions thereof are not necessarily considered in such embodiments to be actual elements of the invention.

Nonetheless, for the purpose of interpreting these terms of reference, reference is herein made to the fourth figure of U.S. Pat. No. 5,676,157 to Kramer, which issued on Oct. 14, 1997 (the "Kramer patent"). In the fourth figure of the Kramer patent, which figure is hereby incorporated herein by reference, the skeletal anatomy of a human hand is illustrated wherein particular bones and joints defined there between are identified. For the purpose of interpreting terms of reference as used herein, the fourth figure of the Kramer patent may be regarded as a dorsal view of a right hand. As shown and as is commonly known, five digits, including a thumb and four fingers, depend from the hand. The three bones of any one of the four fingers, disposed in increasing distance from the hand, are referred to as: the proximal phalange (or proximal phalanx); the middle phalange (or middle phalanx); and the distal phalange (or distal phalanx). A section of a finger may be referred to herein with regard to a particular phalange without ambiguity in that such a section would include the particular bony phalange and the flesh of the finger about the phalange. For example, in typing or in entering data using a keyboard, distal phalange sections of the fingers generally abut and actuate keys of the keyboard without regard to whether distal phalange bones, which are generally surrounded by the flesh of the fingers, ever directly contact the keyboard.

With regard to joints, for each of the four fingers illustrated in the fourth figure of the Kramer patent, a proximal interphalangeal (PIP) joint is defined between the proximal phalange and the middle phalange, and a distal interphalangeal (DIP) joint is defined between the middle phalange and the distal phalange. The thumb, however, having less joints than each of the four fingers, generally includes an interphalangeal joint, indicated in the fourth figure as "THUMB IP," defined between a proximal phalange (or proximal phalanx) and a distal phalange (or distal phalanx). Thus, any recitation herein relating to the "last joint" or "distal joint" of a digit relates equally to any distal interphalangeal joint of a finger and to any interphalangeal joint of a thumb regarding either a left hand or a right hand.

Turning now to the drawings of the present application, dynamic splint assemblies in accordance with preferred embodiments of the invention are illustrated and are described in detail below. It should be furthermore understood that the views found in the accompanying drawings relate to a dynamic splint assembly for a right forearm, wrist, and hand. Nevertheless, the accompanying drawings and the descriptions herein relate equally as well to a dynamic splint assembly for a left forearm, wrist, and hand when a mirror image of the various drawings is considered.

Generally, a dynamic splint assembly of preferred embodiments of the invention includes a volar-based forearm support section and a volar-based hand support section that are joined together. The forearm support section and hand support section have slightly overlapping portions and are permanently or releasably secured together in their overlapping relation by mechanical fasteners. The dynamic splint assembly also includes straps for securing of the dynamic splint to a forearm and hand.

With further general regard to the dynamic splint assembly of preferred embodiments, each of the forearm support section and hand support section exhibits different characteristics and each section is formed from a different material; however, it is contemplated within the scope of the invention that the forearm section and hand support section may constitute integral sections of the same piece so long as each section exhibits the differing characteristics described herein including malleability and resiliency.

The forearm support section, the hand support section, and the straps of a dynamic splint assembly of preferred embodiments, and use thereof, are now described in detail below.

The Forearm Support Section

A dynamic splint assembly 100 in accordance with a preferred embodiment of the invention is illustrated in FIGS. 1-5. The dynamic splint assembly 100 includes a forearm support section 102 that is constructed of a pliable, malleable material, e.g., of a plastic or metal sheet that can be readily bent into a desired, stable configuration by a healthcare professional. For instance, the forearm support section 102 may be stamped, water jet cut or laser cut from a sheet of steel of a desired gauge. It is contemplated, for example, that, in a commercial embodiment, the forearm support section 102 would be manufactured from 19 or 20 gauge steel in a laser cutting, water jet cutting or stamping process. Additionally, the forearm support section 102 is bendable generally along a line 104 for selective orientation of the wrist relative to the forearm when the dynamic splint assembly 100 is donned.

It is contemplated that the dynamic splint assemblies in accordance with the invention may include varying sizes to accommodate varying sizes of forearms, hands, fingers and the like of different users. While a particular size of a dynamic splint assembly or component thereof is not intended to form part of the invention, it is intended that the forearm support section 102 for a particular user be dimensioned to fit beneath a substantial part of the wrist and forearm of the user in covering relation thereto, and extend from the wrist about five inches up the forearm in abutment with volar surface of the forearm.

The forearm support section 102 includes a pair stabilizers 106 positioned on opposite sides of the forearm support section 102 proximal end 108. The stabilizers 106 increase control of forearm positioning, especially when used in conjunction with the forearm straps discussed below. Each of the stabilizers 106 is constructed of a pliable, malleable material, e.g., of a plastic or metal sheet that can be readily bent into a desired, stable configuration by a healthcare professional for abutment with the forearm along a side of the forearm support section. It is contemplated, for example, that, in a commercial embodiment, the stabilizers 106 would be manufactured from 19 or 20 gauge steel in a laser cutting, water jet cutting or stamping process.

The forearm support section 102 further includes a thumb support section 110 that projects from a distal end 112 of the forearm support section 102 and serves to extend beneath and accommodate a thumb. The thumb support section 110 also is constructed of a pliable, malleable material, e.g., of a plastic or metal sheet that can be readily bent into a desired, stable configuration by a healthcare professional for support of the thumb at a desired orientation to the wrist. It is contemplated, for example, that, in a commercial embodiment, the thumb support section 110 would be manufactured from 19 or 20 gauge steel in a laser cutting, water jet cutting or stamping process. Additionally, the thumb support section 110 is bendable generally along line 114 relative to the forearm support section 102.

The thumb support section 110 further includes a thumb restraint section 116 that protrudes from the distal portion of the thumb support section 110. The thumb restraint section 116 insures proper positioning of the thumb in abutment with the thumb support section 110. The thumb restraint section 116 is constructed of a pliable, malleable material, e.g., of a plastic or metal sheet that can be readily bent into a desired, stable configuration by a healthcare professional to act as a restraint or blocking member limiting adductional movement of the thumb away from the thumb support section 110. It is contemplated, for example, that, in a commercial embodiment, the thumb restraint section 116 would be manufactured from 19 or 20 gauge steel in a laser cutting, water jet cutting or stamping process. Additionally, the thumb restraint section 116 is bendable generally along line 118 relative to the thumb support section 110.

In the dynamic splint assembly 100 of FIGS. 1-5, the forearm support section 102, the stabilizers 106, the thumb support section 110, and the thumb restraint section 116 are all formed from an integral piece of planar material in a stamping or laser cutting process. Alternatively, each of the forearm support section 102, the stabilizers 106, the thumb support section 110, and the thumb restraint section 116 may be separately formed and then connected together.

The forearm support section 102 and the thumb support section 110 (and the hand support section 122 described below) each includes a cushioned surface 120, such as a liner or padded material, for abutting, respectively, the volar surfaces of the forearm and the thumb. The cushioned surface also preferably is easily removed from other components of the dynamic splint assembly for cleaning. Such a removable cushioned surface is described in detail below with reference to the dynamic splint assembly of FIGS. 10-16.

The Hand Support Section

The dynamic splint assembly 100 illustrated in FIGS. 1-5 also includes a hand support section 122. The hand support section 122 is constructed of a flexible, resilient material, e.g., of a planar sheet of metal or plastic that will flex from a first, generally planar configuration to a flexed configuration in response to the bending of the fingers and, in doing so, will tend to bias or urge the fingers to return back to the first, generally planar configuration. It is contemplated, for example, that, in a commercial embodiment, the hand support section 122 would be manufactured from between 0.006 inch to 0.010 inch gauge spring steel in a laser cutting, water jet cutting or stamping process. Also, it is intended that the hand support section 122 for a particular user be dimensioned to fit beneath at least a substantial portion of the palm and fingers, i.e., digits 2-5.

The forearm support section 102 and hand support section 122 overlap one another and are connected together such that, when the dynamic splint assembly 100 is properly donned by a user, the connection of the forearm support section 102 and hand support section 122 lies proximate the area of the palm and MCP joints. The connection may be such that the hand support section 122 can be disconnected from the forearm support section 102, whereby another hand support section having a different resistance to flexing may be selected and attached to the forearm support section 102 in order to accommodate differing patient needs. For instance, the two section 102,122 may be joined with an interlocking channel or tab system whereby the flexible hand support section 122 may be readily changed out as needed by someone such as a therapist. Alternatively, the hand support section 122 may be permanently connected to the forearm support section, such as through welding and a permanent adhesive. In the dynamic splint assembly 100, the hand support section 122 is connected to the forearm support section 102 by fasteners (e.g., rivets and/or brads).

As will be apparent to the Ordinary Artisan, the forearm support section 102 is relatively rigid compared to the hand support section 122, yet still somewhat malleable. In contrast to the forearm support section 102, the hand support section 122 has a spring-like resilience. This permits a therapist, for example, to place the wrist in a generally fixed position at a selected degree of flexion and/or extension relative to the forearm. This further permits the therapist to place the thumb in a generally fixed position at a selected degree of palmer abduction, adduction, flexion, and extension.

The Straps

The dynamic splint assembly 100 includes a plurality of straps that are used to respectively secure the forearm support section 102 and the hand support section 122 to the forearm and to the hand. In particular, the dynamic splint assembly 100 illustrated in FIGS. 1-5 includes six straps 124, 126, 128, 130, 132, 133 of various lengths and widths. Each of the straps preferably includes at least one area of hook-and-loop material, i.e., at least an area of hooks or at least an area of loops, for releasable fastening of the strap. Each strap may releasably fasten to itself or to another component of the dynamic splint assembly, such as a mating hook-and-loop material adhered to the forearm support section or to the hand support section.

Straps 124, 126 are used to secure the forearm support section 102 to the forearm and each has sufficient length for encircling the forearm. Specifically, strap 124 wraps about the forearm support section 102 at the proximal end 108 thereof in covering relation to the stabilizers 106 for further securing the stabilizers 106 in abutment with the forearm, which tends to insure proper positioning of the dynamic splint assembly 100 on the forearm. Strap 126 wraps about the forearm support section 102 in encircling the forearm in an area between the stabilizers 106 and the hand support section 122.

Straps 128, 130 are used to secure the hand support section 122 to the fingers of the hand. Strap 128 has sufficient length for encircling the index, middle and ring fingers, and strap 130 has sufficient length for encircling the pinkie or little finger. Accordingly, strap 128 is used to encircle the index finger, the middle finger, and the ring finger (i.e., digits 2, 3, and 4), and strap 130 is used to encircle the little finger.

In order to facilitate use of straps 128, 130 to secure the fingers, and to provide a more intimate fit of the straps 128, 130 with the fingers, the hand support section 122 includes cutouts for receiving the straps 128, 130. In particular, the hand support section 122 includes a cutout comprising slot 134 through which strap 128 and strap 130 pass through. The hand support section 122 further includes, on a radial side thereof, a cutout comprising a side indentation 136 that receives the strap 128 in its encircling of the index finger, the middle finger, and the ring finger. Similarly, the hand support section 122 includes on an ulnar side thereof a cutout comprising a side indentation 138 that receives the strap 130 in its encircling of the little finger. The slot 134 and side indentations 136, 138 each have a sufficient extent to allow for proximal/distal adjustments of the straps 128, 130 in order to accommodate a variety of finger lengths.

When used as intended, strap 128 preferably extends from the volar side of the hand support section 122, passes up through the slot 134, over the dorsal side of the ring, middle, and index fingers on the proximal phalanx thereof in proximity to the PIP joints, and then around the radial side of the hand support section 122 within side indentation 136, and back to the volar side of the hand support section 122.

Similarly, when used as intended, strap 130 preferably extends from the volar side of the hand support section 122, passes up through the slot 134, over the dorsal side of the little finger on the proximal phalanx in proximity to the PIP joint, and then around the ulnar side of the hand support section 122 within side indentation 138, and back to the volar side of the hand support section 122.

In addition to strap 128, an additional strap (not shown) may be provided in order to further secure the index finger, the middle finger, and the ring finger. In this respect, the slot 134 and side indentation 136 each further have a sufficient extent to allow for this additional strap to be used in parallel with strap 128. In this case, it is intended that this additional strap would extend from the volar side of the hand support section 122, up through the slot 134, over the dorsal side of the ring, middle, and index fingers on the middle phalanx thereof in proximity to the DIP joints, and then around the radial side of the hand support section 122 within side indentation 136, and back to the volar side of the hand support section 122.

Strap 132 is used to secure the hand support section 122 to the volar portion of the hand and has sufficient length for encircling the volar portion of the hand and the dorsum of the hand. Furthermore, in order to facilitate use of strap 132 and provide a more intimate fit with the hand, the hand support section 122 in conjunction with the forearm support section 102 define a cutout for receiving the strap 132. In particular, a cutout comprising a side indentation 140 located on the ulnar side of the hand support section 122 and forearm support section 102 receives the strap 132 as it wraps around the ulnar side of the dynamic splint assembly 100. The side indentation 136 on the radial side of the hand support section 122, which receives strap 128, also receives strap 132 as it wraps about the radial side of the dynamic splint assembly 100. When used as intended, strap 132 preferably from the volar side of the hand support section 122 proximate the palm of the hand, around the dorsum of the hand just proximal to the MCP joints of the fingers, and then back to the volar side of the hand support section 122 proximate the palm of the hand.

Strap 133 is used to secure the thumb to the thumb support section 110 and has sufficient length for encircling the thumb. Furthermore, in order to facilitate use of strap 133, the thumb support section 110 defines cutouts for receiving the strap 133 on opposite sides of the thumb support section 110. In particular, a cutout comprising a side indentation 142 located on the ulnar side of the thumb support section 110 receives the strap 133 as it wraps there around, and a cutout comprising a side indentation 144 located on the radial side of the thumb support section 110 receives the strap 133 as it wraps there around. When used as intended, strap 133 preferably extends from the volar side of the thumb support section 110, wraps around the ulnar side of the thumb support section 110 within side indentation 142, over the dorsal surface of the thumb on the proximal phalanx in proximity to the IP joint, around the radial side of the thumb support section 110 within side indentation 144, and back to the volar side of the thumb support section 110.

As will be appreciated from the foregoing description of the arrangement of the straps, the particular arrangement of the straps and their disposition relative to the various digits and joints is intended to keep the thumb and fingers from pulling out of the straps during use. Additionally, the volar surfaces of the straps (which contact the hand) preferably include non-slip (high friction) surfaces that abut the fingers and thumb for further keeping the thumb and fingers from pulling out of the straps.

Figure 6A:
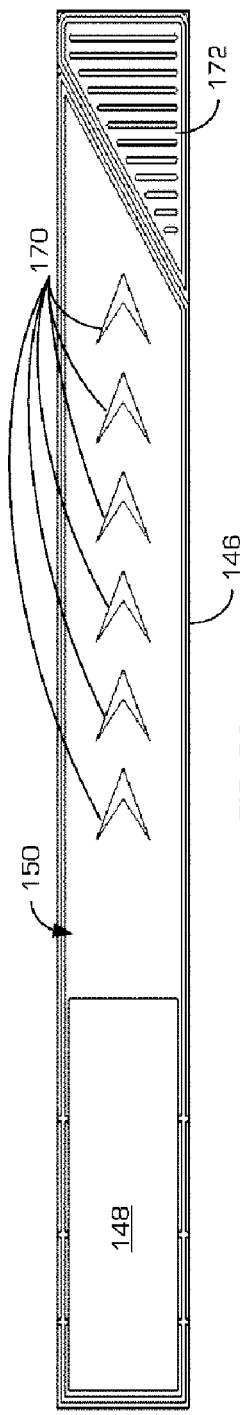
FIGS. 6A-6D each is a top plan view of a strap of a dynamic splint assembly in accordance with a contemplated commercial embodiment of the invention.

Straps for a contemplated commercial embodiment of the invention are illustrated in FIGS. 6A, 6B, 6C, and 6D. In FIG. 6A, the strap 146 represents the straps for securing the forearm support section to the forearm (and is representative of straps 124 and 126 illustrated in FIG. 4). Strap 146 includes an area 148 of hook-and-loop material adhered to the front side 150 of the strap 146 as well as an area (not shown) of mating hook-and-loop material on the back side. Strap 146 preferably is 12.0 inches long and 1.75 inches wide.

Figure 4:
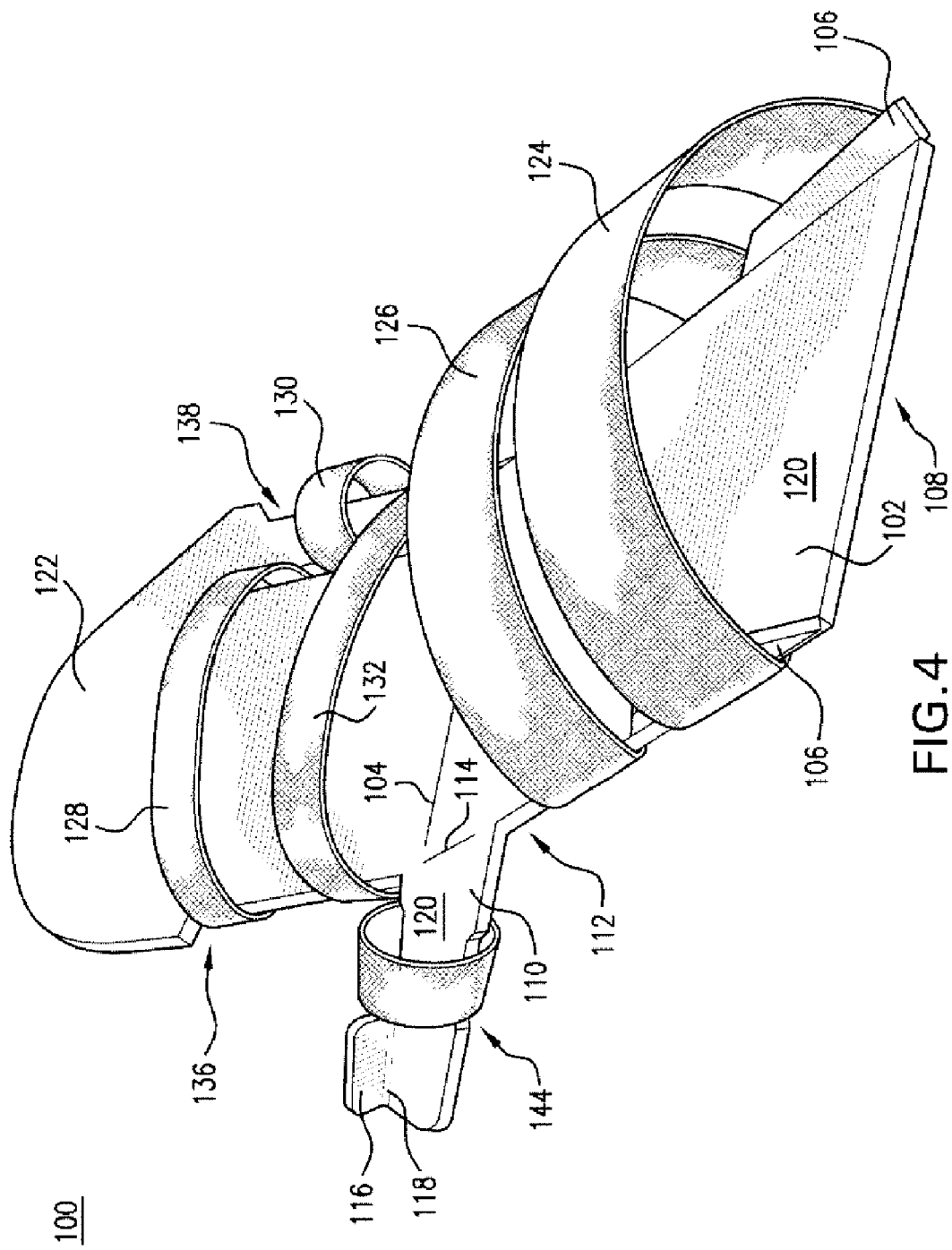
FIG. 4 is a back perspective view of a rear of the dynamic splint assembly of FIG. 1.
Figure 5:
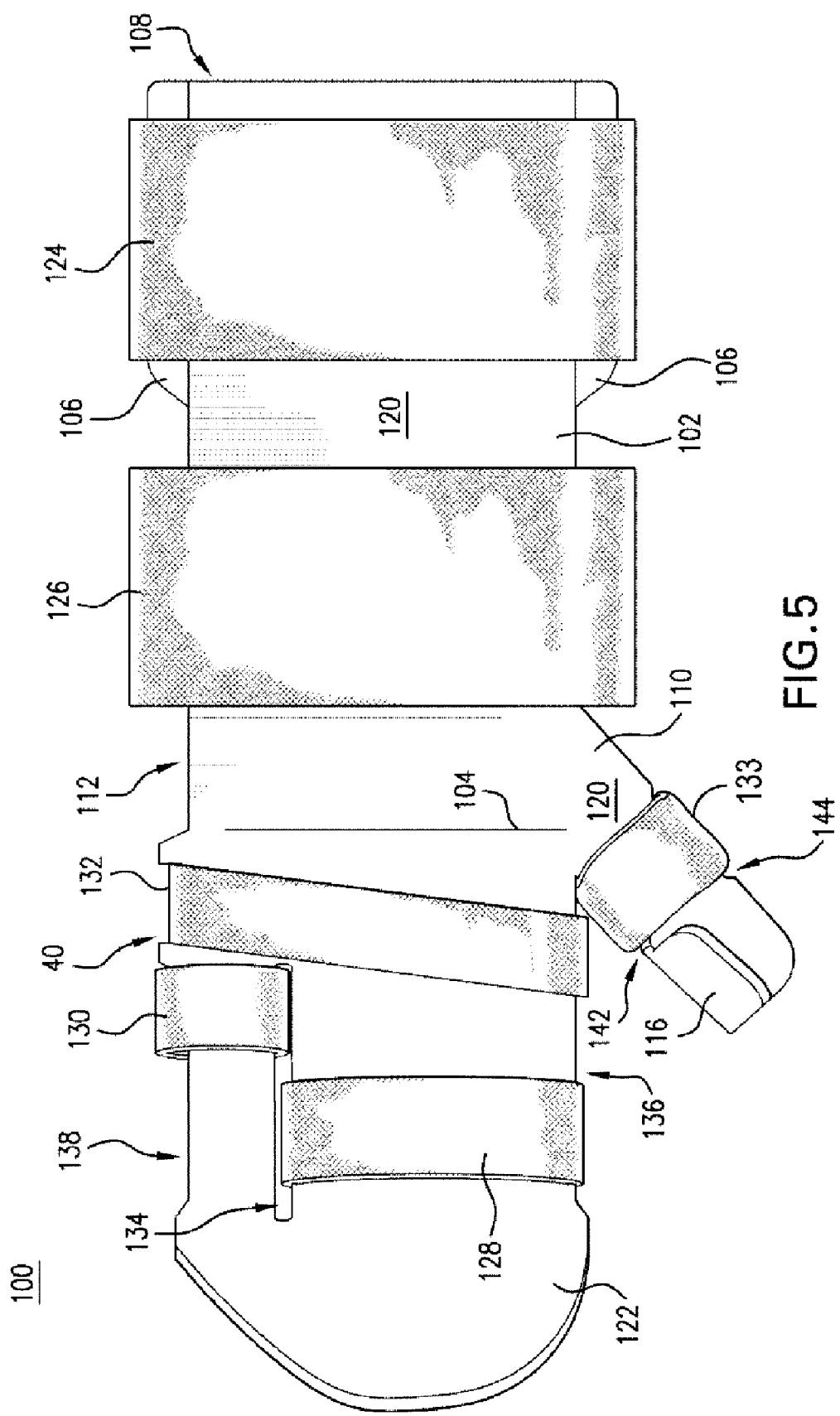
FIG. 5 is a top plan view of the dynamic splint assembly of FIG. 1.
Figure 6B:
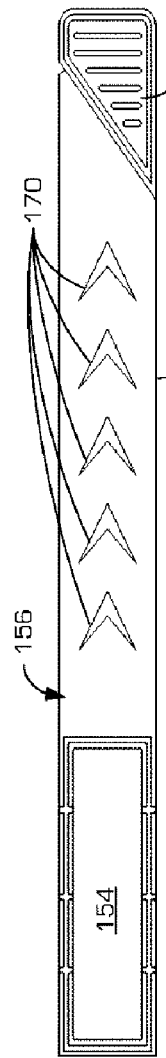

In FIG. 6B, the strap 152 represents the strap for securing the group of three fingers (digits 2, 3, and 4) to the hand support section (and is representative of strap 128 illustrated in FIG. 4). Strap 152 includes an area 154 of hook-and-loop material adhered to the front side 156 as well as an area (not shown) of mating hook-and-loop material on the back side. Strap 152 preferably is 9.0 inches long and 1.0 inch wide.

Figure 6C:
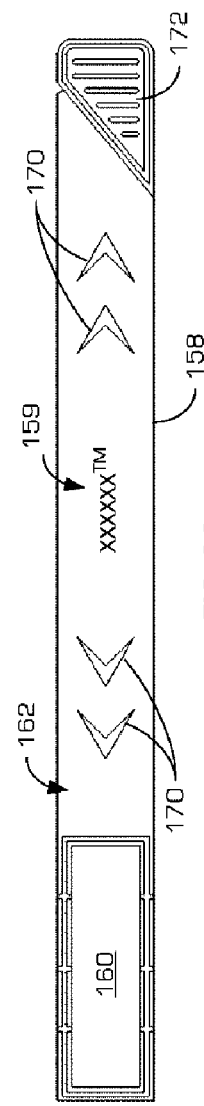

In FIG. 6C, the strap 158 represents the strap for securing the palmer portion of the hand and the dorsum of the hand to the hand support section (and is representative of strap 132 illustrated in FIG. 4). Strap 158 includes an area 160 of hook-and-loop material adhered to the front side 162 and an area (not shown) of mating hook-and-loop material on the back side. Strap 158 further includes an area 159 on the front side 162 for depiction of indicia, such as a trademark representing a brand for a dynamic splint assembly. Strap 158 preferably is 11.0 inches long and 1.0 inch wide.

Figure 6D:
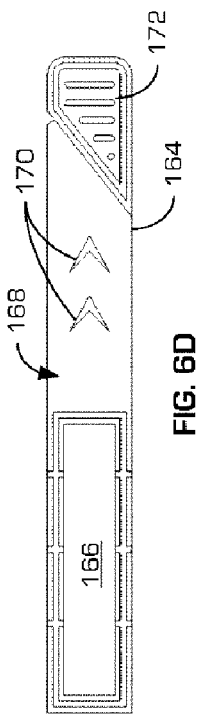

Finally, in FIG. 6D, the strap 164 represents both the strap for securing the little finger (digit 5) to the hand support section and the strap for securing the thumb (digit 1) to the hand support section (and is representative of straps 130, 133 in FIG. 4). Strap 164 includes an area 166 of hook-and-loop material adhered to the front side 168 and an area (not shown) of mating hook-and-loop material on the back side. Strap 164 preferably is 5.5 inches long and 0.75 inches wide.

Each of the straps 146, 152, 158, 164 is formed from a flexible material that is tensionable and comprises silicone and/or TPR (thermoplastic rubber), but preferably does not include latex. Each of the straps 146, 152, 158, 164 further includes raised chevrons 170 and ribs 172 formed, printed, or adhered to the front side thereof. The raised chevrons 170 and, in particular, the raised ribs 172 provide advantageous gripping surfaces for tensioning of the straps.

Use of the Dynamic Splint Assembly

In using the dynamic splint assembly 100, a healthcare worker, for example, shapes the forearm support section 102 as desired by bending the forearm support section 102 along line 104 for disposition proximate the wrist so that the wrist will be positioned in a desired orientation to the forearm support section 102 when the dynamic splint assembly 100 is donned. This bending of the forearm support section 102 further positions the hand support section 122 in an initial orientation to the forearm support section 102. Each stabilizer 106 further is bent upwardly relative to the forearm support section 102 for abutment with the forearm when the dynamic splint assembly 100 is donned. The healthcare worker then shapes the thumb support section 110 as desired by bending the thumb support section along line 114 for disposition proximate the thumb so that the thumb will be positioned in a desired orientation to the forearm support section 102 when the dynamic splint assembly 100 is donned. The thumb restraint section 116 further is bent upwardly along line 118 relative to the thumb support section 110, which further insures proper positioning of the thumb in abutment with the thumb support section 110.

Figure 7:
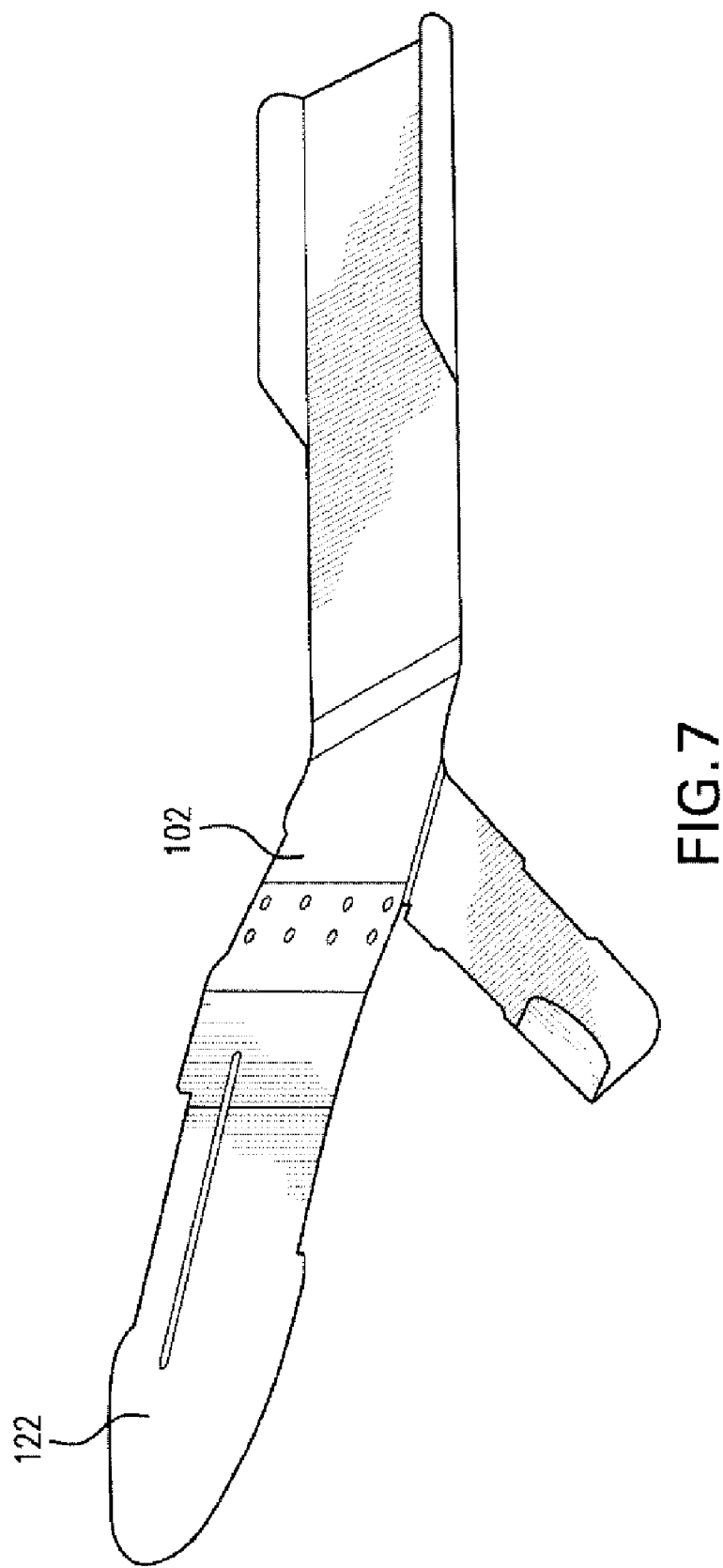
FIG. 7 an elevational view of a left side of a forearm support section and a hand support section of a dynamic splint assembly for a right hand in accordance with an embodiment of the invention, wherein the hand support section is disposed in a first extended position.
Figure 8:
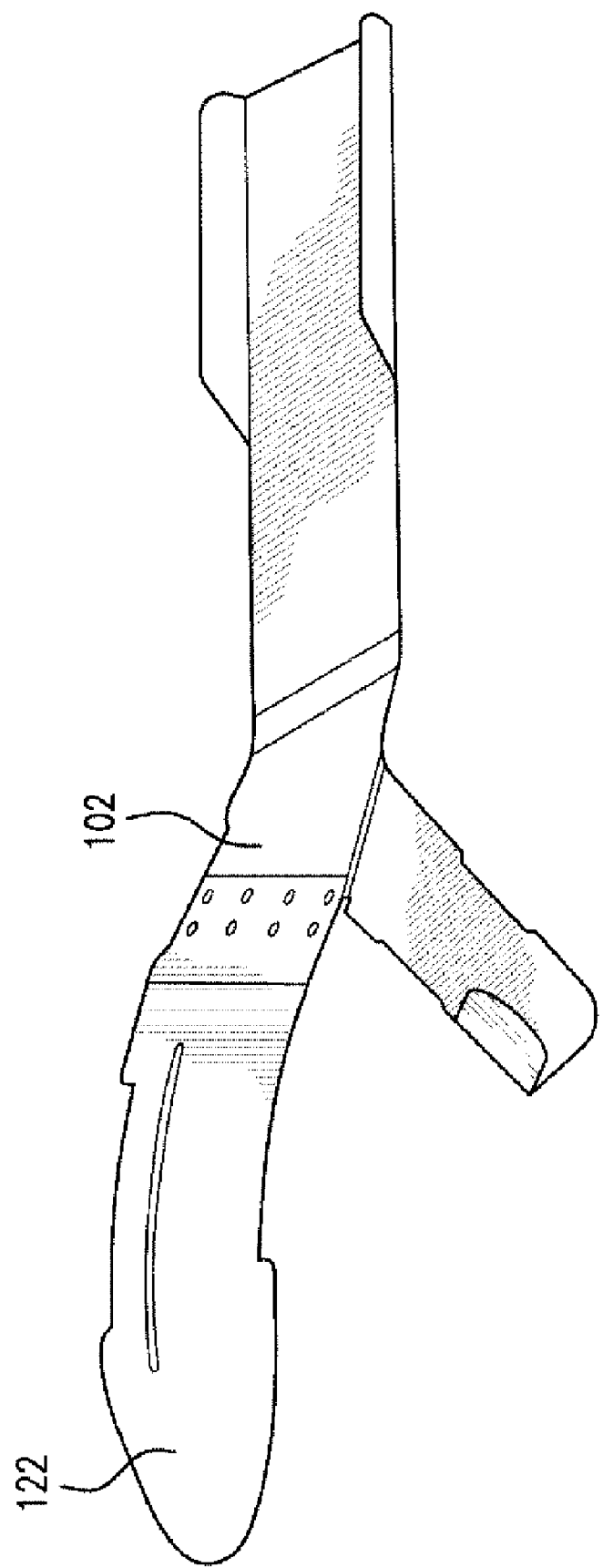
FIG. 8 an elevational view of the left side of the forearm support section and the hand support section of FIG. 7, wherein the hand support section is disposed in a second, flexed position relative to the first extended position of FIG. 7.
Figure 9:
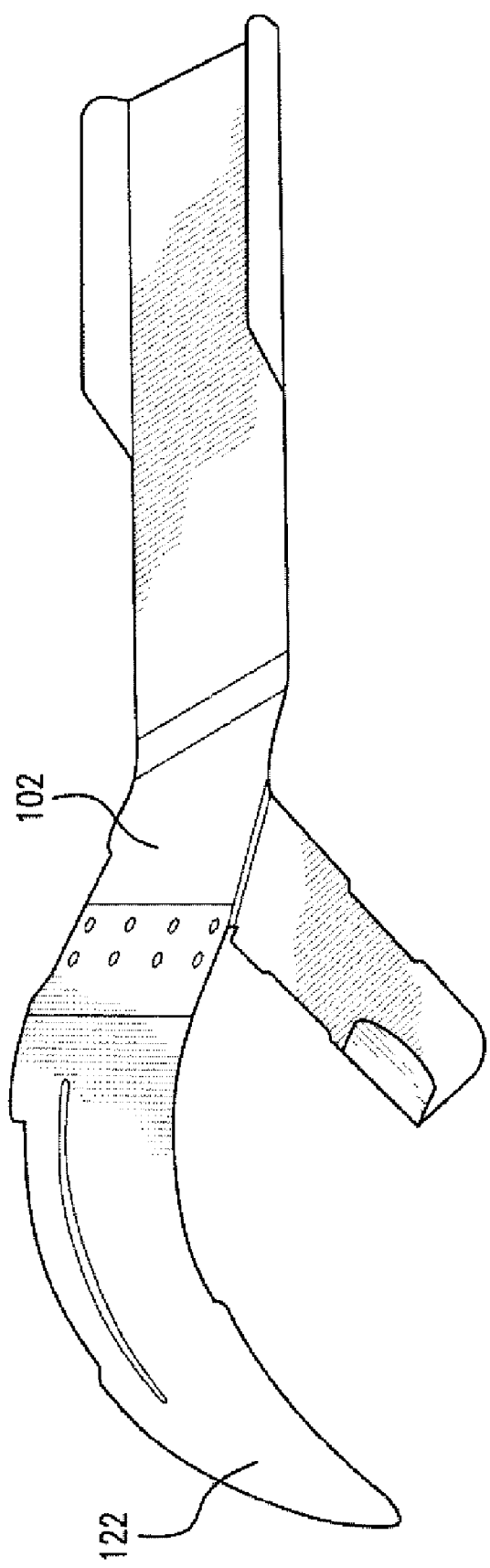
FIG. 9 an elevational view of the left side of the forearm support section and the hand support section of FIG. 7, wherein the hand section is disposed in a third, flexed position relative to the second, flexed position of FIG. 8.

The dynamic splint assembly 100 then is secured to the volar surfaces of the forearm and hand with the straps 124, 126, 128, 130, 132, 133. When properly secured, the hand support section 122 will flex downwardly during flexion of the fingers. During extension of the fingers from flexion, the hand support section 122 preferably returns to the initial position, which may be an extended, unflexed or slightly flexed state depending on the original positioning of the dynamic splint and the patient specific presentation. FIGS. 7-9 illustrate this bending motion of a hand support section. In particular, FIG. 7 illustrates a hand support section 122 disposed in an initial position relative to a forearm support section 102; FIG. 8 illustrates the hand support section 122 disposed in a second intermediate flexed position relative to the forearm support section 102; and FIG. 9 illustrates the hand support section 122 disposed in a third, further flexed position relative to the forearm support section 102.

It will be appreciated that, during flexion of the fingers, and while the fingers are flexed, the hand support section applies a counter force urging the fingers toward an unflexed or extended condition that results in a low load, long duration stretch. Furthermore, the resulting counter force preferably increases as the degree of bending of the hand support section increase, due to the elastic characteristics of the material of the hand support section. It further will be appreciated that, when the dynamic splint assembly 100 is utilized with a neurologically impaired hand presenting with hypertonicity, this resulting counter force enables the fingers to reach an substantially extended position that otherwise might not be possible. Use of the dynamic splint assembly 100 further assists in rehabilitation and therapy of such a hand.

Accordingly, dynamic splint assemblies of preferred embodiments of the invention preferably are designed for use with the neurologically impaired hands. In this respect, each dynamic splint assembly preferably is used to hold an impaired wrist in varying degrees of flexion and/or extension, hand, and fingers generally in an extended position, with the thumb at varying degrees of palmer adduction, abduction, flexion and or extension, depending on patient specific needs. Ideally, the dynamic splint assembly positions the impaired wrist and hand in an extended position and urges the long finger flexors, and long thumb flexor and adductors, in an extended position resulting in a low load long duration stretch.

Furthermore, the ability to interchange hand support sections (which is provided by dynamic splint assemblies having a hand support section that is removably attached to the forearm support section) permits the application of staged, increased resistances to flexion by the fingers as therapy and rehabilitation progress. Providing dynamic splint assemblies with varying degrees of resistances further permits one to match the soft tissue shortening and spasticity—as well as hypertonicity—of an individual's fingers and/or thumb.

Layered Components of a Preferred Embodiment

Figure 10:
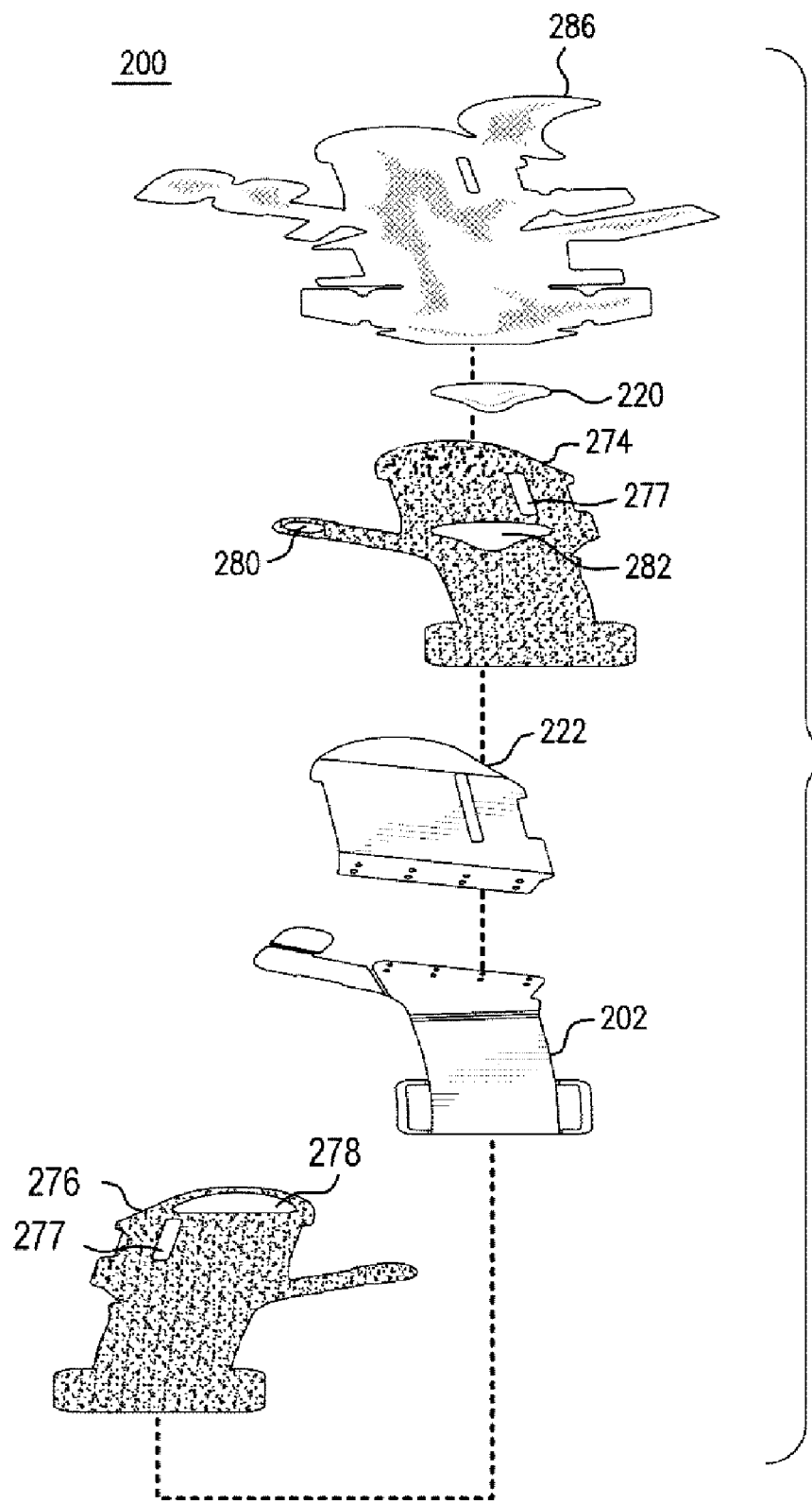
FIG. 10 is an exploded view of a dynamic splint assembly for a right hand in accordance with another embodiment of the invention.
Figure 11:
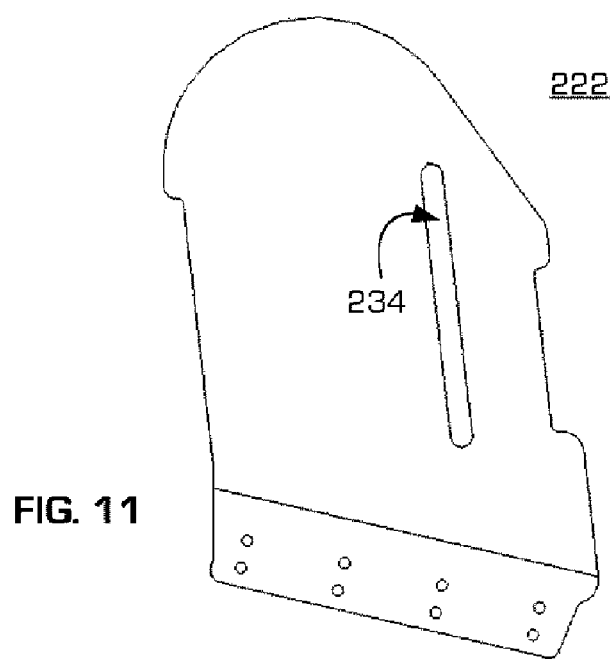
FIG. 11 is a plan view of a dorsal side (for engagement with the volar side of the fingers of a hand) of a hand support section of the dynamic splint assembly of FIG. 10.
Figure 12:
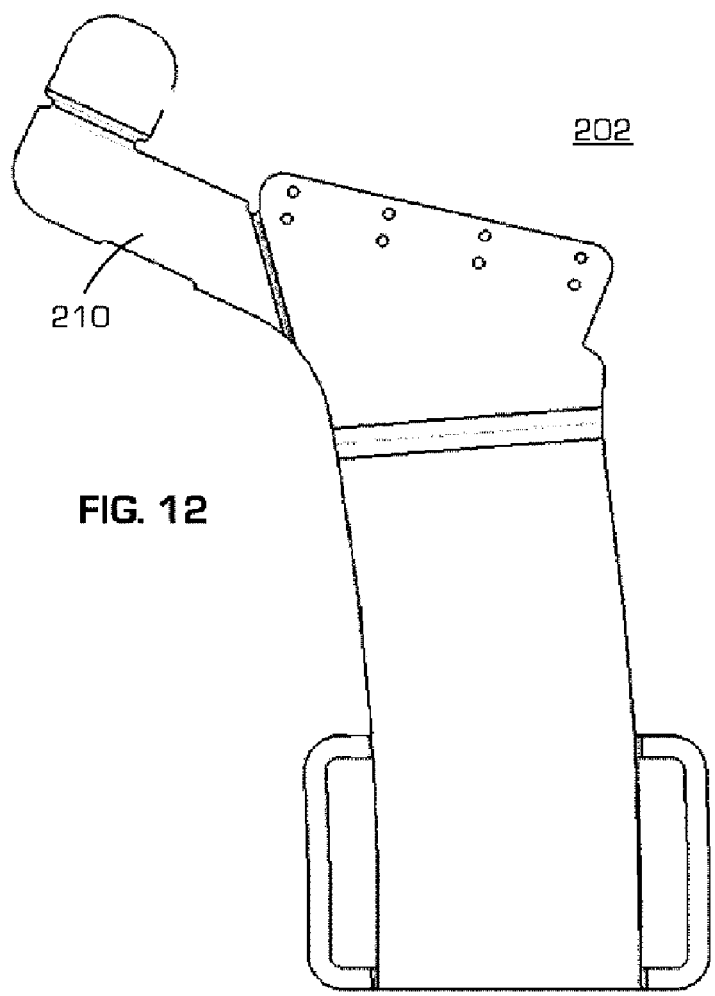
FIG. 12 is a plan view of a dorsal side (for engagement with the volar side of a forearm) of a forearm support section of the dynamic splint assembly of FIG. 10.
Figures 13, 14:
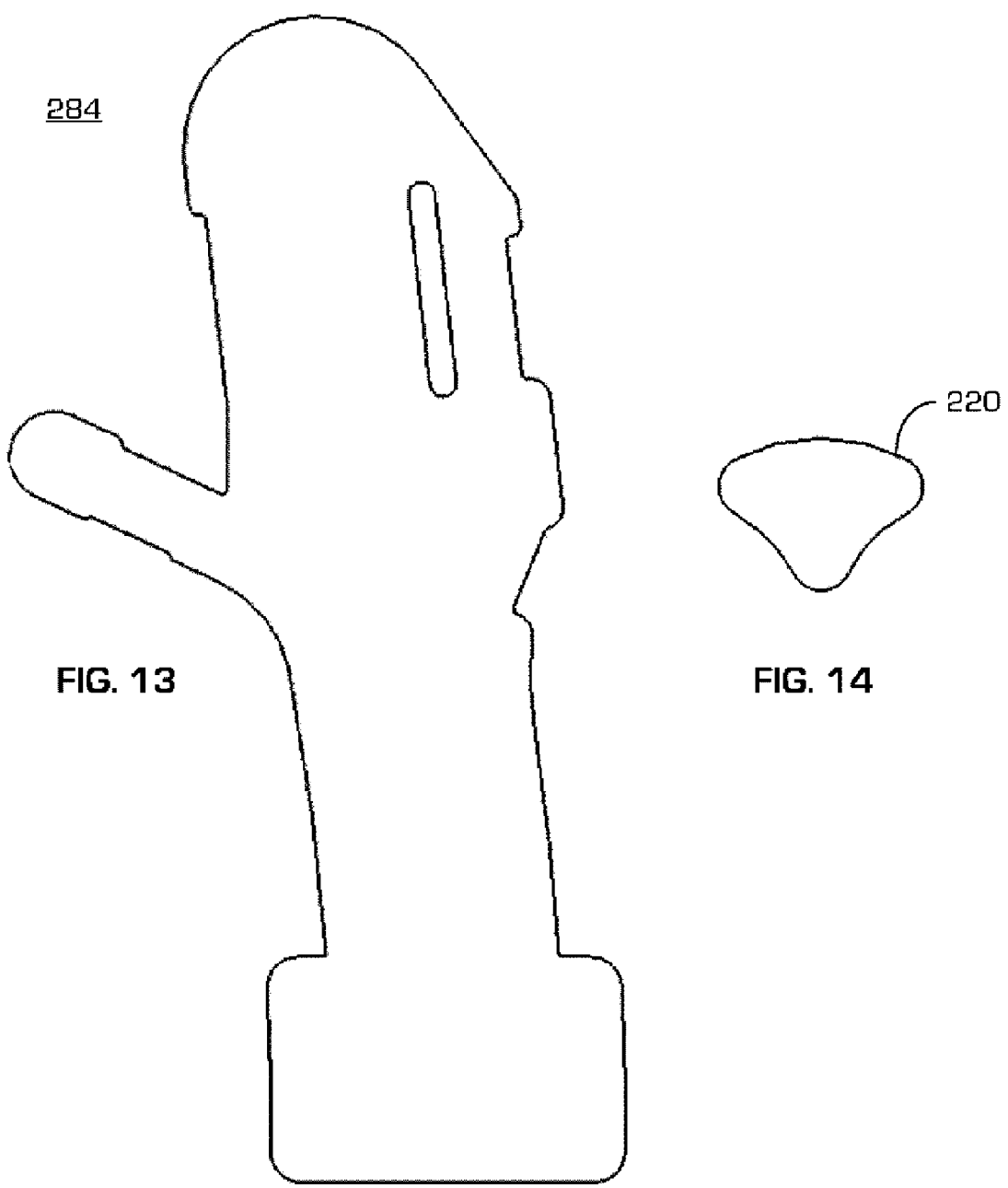
FIG. 13 is an illustration of a profile of the top and bottom liners of the dynamic splint assembly of FIG. 10.
FIG. 14 is a top plan view of a pad of the dynamic splint assembly of FIG. 10.

FIG. 10 illustrates an exploded view of a dynamic splint assembly 200 in accordance with another preferred embodiment of the invention. The components of the dynamic splint assembly 200 include a forearm support section 202 and hand support section 222, each like the forearm support section 102 and hand support section 122 of the dynamic splint assembly 100 of FIGS. 1-5. The hand support section 222 also is illustrated in FIG. 11 and the forearm support section 202 also is illustrated in FIG. 12.

The components of the dynamic splint assembly 200 also include a top liner 274 and bottom liner 276. Each liner 274, 276 preferably includes a profile 284 (represented in FIG. 14) that corresponds to and registers with the profile of the forearm support section 202 (including the thumb support section 210) combined with the hand support section 222. Furthermore, liner 274 further includes areas of hook-and-loop material on a dorsal side surface thereof, and liner 276 further includes areas of hook-and-loop material on a volar side surfaces thereof. In this respect, each area of hook-and-loop material preferably corresponds to the entire surface of the respective side of the liner 274,276.

The top liner 274 and bottom liner 276 are similar pieces that are utilized as different components. As such, both liners 274 and 276 define an opening 277 that corresponds to slot 134. The top liner 274 further has an opening 280 in the distal area of the thumb support section 210, and the bottom liner 276 further has an opening 278 in the distal area of the hand support section 222.

Figure 15:
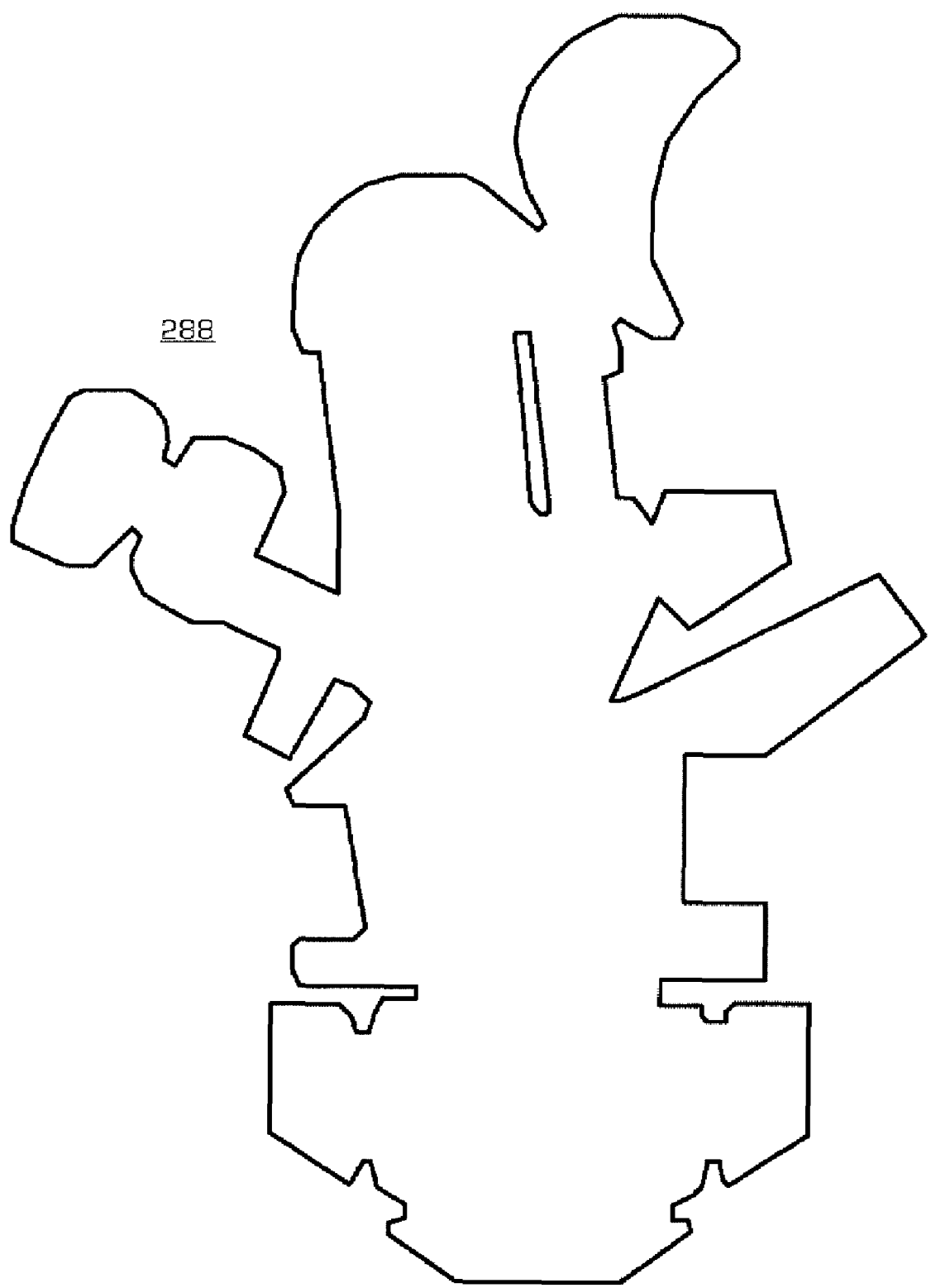
FIG. 15 is a profile of the covering of the dynamic splint assembly of FIG. 10.

The components of the dynamic splint assembly 200 also include a pad 220 (also illustrated in FIG. 14B) and a covering 286 (the planar profile 288 of which is illustrated in FIG. 15). The pad 220 provides additional padding and serves as a cushion maintaining the palmer arch of the hand. Additional pads (not shown) optionally may be included in the dynamic splint assembly 200, with the pad 221 for providing additional cushioning support of the fingers and the thumb.

The covering 286 is constructed from a pliable, padded material and serves as the exterior, dorsal surface of the dynamic splint assembly 200. The material of the covering 286 also preferably allows air and moisture to circulate and wick away from the skin of the hand and, preferably, is about 0.125 inches thick. In an alternative construction (not shown), the covering may include compression molded padding that forms an integral part of the covering thereby obviating the need for a separate pad.

In a contemplated commercial embodiment, the covering comprises stretchable synthetic fabric such as that currently available under the federally registered trademark BREATH-O-PRENE and synthetic elastomeric fibers such as those manufactured by DuPont under the federally registered trademark LYCRA. Neoprene also may be used. The volar side of the covering 286 further preferably includes an area of hook-and-loop material that is capable of interlocking engagement with the areas of hook-and-loop material on both sides of the liners 274, 276.

In order to further prevent slipping of the fingers, thumb, or hand when the dynamic splint assembly 200 is donned and one or more digits are flexed, the covering 286 also preferably includes a non slip (high friction) material adhered, screened, printed, or otherwise affixed in areas for abutment with the fingers, thumb of the hand. Such areas may include chevrons (not shown) that are silk screened onto the covering 286.

In combining the components of the dynamic splint assembly 200, the hand support section 222 preferably is connected with brads to the forearm support section 202. Thereafter, the top liner 274 is adhered (preferably using an adhesive) to the dorsal surface of the combined sections 202, 222 and the bottom liner 276 is adhered (preferably using an adhesive) to the volar surface of the combined sections 202, 222 with the profiles of the liners in registry with that of the combined sections 202, 222. Furthermore, the openings 277 of the respective liners 274, 276 preferably register with the slot 234 of the hand support section 222.

Thereafter, the pad 220 is positioned over the combined sections 202, 222 on the top liner 274, and the covering 286 is disposed over the top liner 274 and wrapped around the combined sections 202, 222 to engage the bottom liner 276. In so doing, the areas of hook-and-loop material on the volar surface of the covering 286 preferably releasably engage the areas of hook-and-loop material on the top and bottom liners 274, 276. The covering 286 or portions thereof further may be sewn creating pockets that further secure attachment to the hand and forearm sections.

The covering 286 helps maintain the pad 220 in its proper position between the top liner 274 and the covering 286 for support of the palmer arch when the dynamic splint assembly 200 is donned. A top plan view of the covering 286 releasably attached to form the assembled dynamic hand splint 200 is illustrated in FIG. 16A, a bottom plan view thereof is illustrated in FIG. 16B, and a perspective view of the bottom thereof is illustrated in FIG. 16C.

It will be appreciated that, because the covering 286 is releasably attached to the top and bottom liners 274, 276 by way of mating engagement between the areas of hook-and-loop material, the covering 286 may be temporarily removed from the dynamic splint assembly 200 for maintenance, such as cleaning, or for replacement. Furthermore, in this regard, the covering 286 preferably is washable, and may be treated with an antibacterial, antifungal, and anti odor agents.

Alternative Embodiments of the Invention

Certain modifications and improvements will occur to those skilled in the art upon reading of the foregoing description. It should be understood that all such modifications and improvements have not been explicitly set forth herein for the sake of conciseness and readability but are indeed within the scope of the invention.

Figure 17:
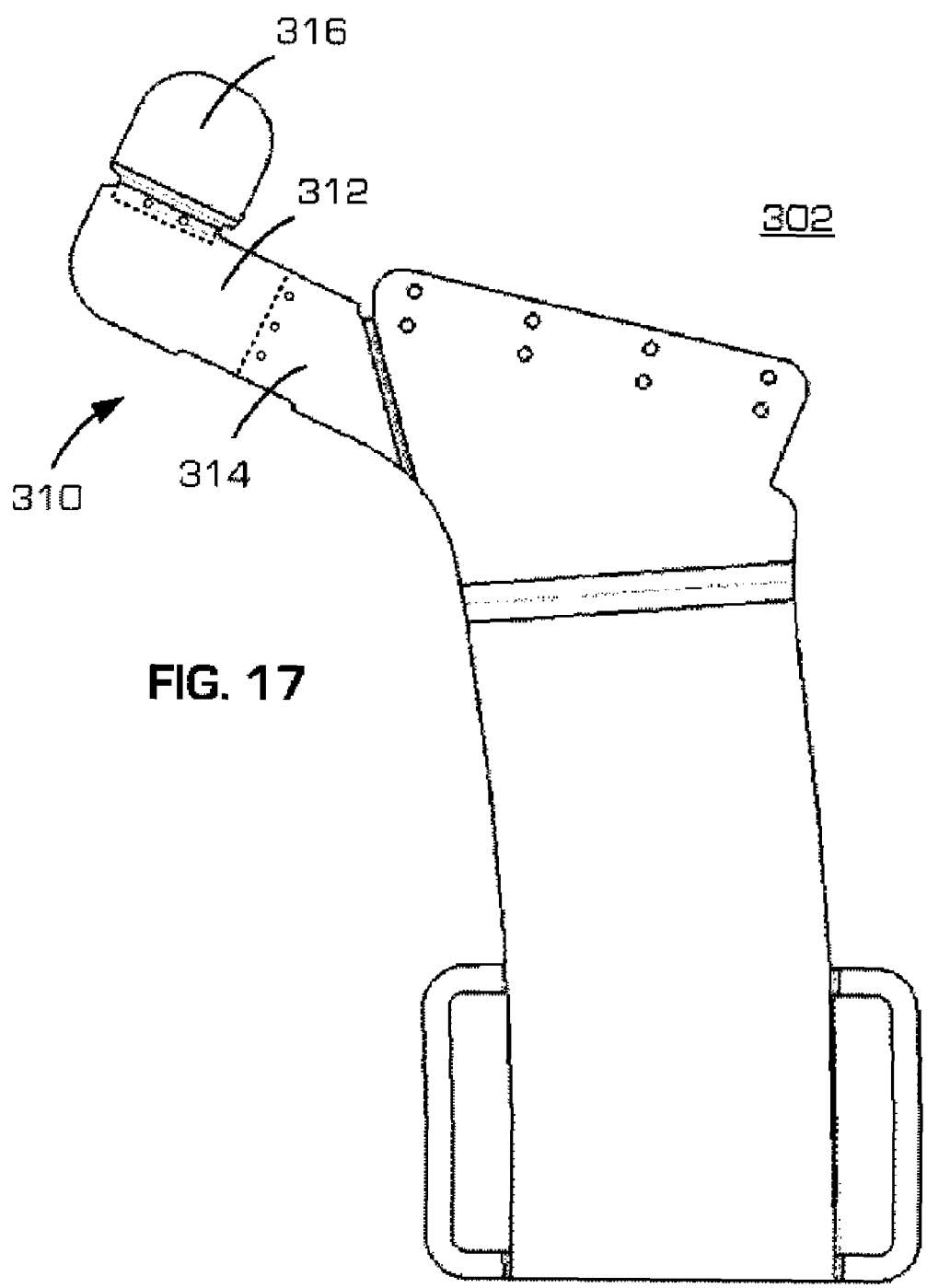
FIG. 17 is a plan view of a dorsal side (for engagement with the volar side of a forearm) of a forearm support section of a dynamic splint assembly of an alternative embodiment.

For example, in an alternative embodiment of the invention, a thumb support section 310 includes a distal thumb support section 312 that, itself, preferably comprises a separate component as shown in FIG. 17. The distal thumb support section 312 is secured to a proximal thumb support section 314 in similar manner as the hand support section 122 is secured to the forearm support section 102 in the dynamic splint assembly 100 of FIGS. 1-5. Also like the hand support section 122, the distal thumb support section 312 preferably is constructed of a flexible, resilient material, e.g., of a planar sheet of metal or plastic that will flex from a first, generally planar configuration to a flexed configuration in response to the bending of the thumb and, in doing so, will tend to bias or urge the thumb to return back to an extended position such that the thumb support section would return back to the first, generally planar configuration. It is contemplated, for example, that, in a commercial embodiment, the distal thumb support section 312 would be manufactured from between 0.006 inch to 0.010 inch gauge spring steel in a laser cutting, water jet cutting or stamping process. The proximal thumb support section 314 would be made of the malleable material as in the thumb support section 110 in the dynamic splint assembly 100 of FIGS. 1-5. This alternative embodiment further would include a thumb restraint section 316 connected to the distal thumb support section 314 in similar manner as the hand support section 122 is secured to the forearm support section 102 in the dynamic splint assembly 100 of FIGS. 1-5. Such an alternative dynamic splint assembly would be beneficial, for example, in therapeutic and rehabilitative exercises by a thumb experiencing hypertonicity.

Indeed, another dynamic splint assembly in accordance with another alternative embodiment of the invention may include only the thumb support section being constructed of a flexible, resilient material for rehabilitation and therapy of just the thumb when the fingers do not require similar treatment. In this case, the hand support section may be formed of a pliable, malleable material similar to the forearm support section 102 of the dynamic splint assembly 100 of FIGS. 1-5.

What is claimed is:

1. A dynamic splint assembly for a hand, comprising:
   (a) a forearm support section configured to abut the volar side of a forearm and span a wrist; and
   (b) a hand support section connected to and extending from an end of the forearm support section, the hand support section configured to abut the volar side of the hand including at least the volar side of the length of one finger;
   (c) wherein,
      (i) the hand support section comprises a resilient material that, in response to bending, such as during flexion of an abutted finger, generates a continuous restoring force in opposition to such bending, whereby an abutted finger in flexion is urged toward extension, and
      (ii) the forearm support section comprises a malleable material that does not generate, in response to bending, a continuous restoring force in opposition to such bending, whereby a wrist may be selectively oriented in one of a plurality of fixed dispositions having varying degrees of flexion and extension relative to a forearm when the dynamic splint assembly is donned.

2. The dynamic splint assembly of claim 1, wherein the hand support section is releasably connected to the forearm support section such that the hand support section may be readily substituted with another hand support section comprising a material having a different resiliency.

3. The dynamic splint assembly of claim 1, wherein the forearm support section comprises protuberances on opposite ulnar and radial sides thereof proximate an end of the forearm support section, whereby each protuberance may be bent at a selective angle relative to the forearm support section for stabilization of the proximal end of the forearm support section on the forearm.

4. The dynamic splint assembly of claim 1, further comprising a plurality of straps for securing the connected forearm support section to the forearm and the hand support section to a hand.

5. The dynamic splint assembly of claim 4, wherein the hand support section defines a slot having an extent sufficient for three of the straps to concurrently extend there through.

6. The dynamic splint assembly of claim 4, wherein at least one of the straps comprises a non-slip material on a volar side thereof for frictional engagement with the skin of the hand and fingers.

7. The dynamic splint assembly of claim 4, wherein the hand support section defines a side indentation along an ulnar side thereof for receipt and retention therein of one of the straps when wrapped around the ulnar side of the hand support section, the strap configured for wrapping around the little finger of the hand.

8. The dynamic splint assembly of claim 4, wherein the hand support section defines a side indentation along a radial side thereof for receipt and retention therein of at least one of the straps when wrapped around the radial side of the hand support section, the strap configured for wrapping around the index finger of the hand.

9. The dynamic splint assembly of claim 4, wherein the hand support section and the forearm support section when connected together define a side indentation along an ulnar side thereof for receipt and retention therein of one of the straps when wrapped around the ulnar side of the hand support section, the strap configured for wrapping around the palmer portion and the dorsum of the hand.

10. The dynamic splint assembly of claim 4, wherein the forearm support section further comprises a thumb support section configured to abut the volar side of the length of the thumb of the hand, and wherein the thumb support section defines side indentations along opposite sides thereof for receipt and retention therein of one of the straps when wrapped around the ulnar and radial sides of the thumb support section, the strap configured for wrapping around the thumb of the hand.

11. A method for donning a dynamic splint assembly for a hand, comprising the steps of:
   (a) providing a dynamic splint assembly comprising,
      (i) a forearm support section configured to abut the volar side of a forearm and span a wrist, and
      (ii) a hand support section connected to and extending from an end of the forearm support section, the hand support section configured to abut the volar side of the hand including at least the volar side of the length of one finger,
      (iii) wherein,
         (A) the hand support section comprises a resilient material that, in response to bending, such as during flexion of an abutted finger, generates a continuous restoring force in opposition to such bending, whereby an abutted finger in flexion is urged toward extension, and
         (B) the forearm support section comprises a malleable material that does not generate, in response to bending, a continuous restoring force in opposition to such bending, whereby a wrist may be selectively oriented in one of a plurality of fixed dispositions having varying degrees of flexion and extension relative to a forearm when the dynamic splint assembly is donned;

(b) bending the forearm support section such that a wrist is oriented in a selected one of a plurality of fixed dispositions having varying degrees of flexion and extension relative to a forearm when the dynamic splint assembly is donned;

(c) positioning the forearm support section such that the forearm support section abuts the volar side of the forearm and such that the forearm support section spans the wrist with the wrist oriented in the selected fixed disposition of flexion and extension relative to the forearm support section;

(d) positioning the hand support section such that the hand support section abuts the volar side of the hand including at least the volar side of the length of a finger and such that the hand support section generates a continuous restoring force during flexion of the abutted finger whereby the abutted finger in flexion is urged toward extension;

(e) securing the forearm support section on the forearm with a strap; and (f) securing the hand support section on the hand with a strap.

12. The method of claim 11, wherein the step of securing the hand support section on the hand with a strap comprises positioning a strap to extend through a slot formed in the hand support section that extends proximate the radial side of the little finger and proximate the ulnar side of the ring finger, over the index, middle, and ring fingers, and around the radial side of the hand support section.

13. The method of claim 12, wherein the step of securing the hand support section on the hand with a strap comprises positioning a strap to extend through the slot formed in the hand support section, over the little finger, and around the ulnar side of the hand support section, whereby at least two straps extend through the slot.

14. The method of claim 12, wherein the strap extending around the radial side of the hand support section abuts the proximal phalanx of each of the index, middle, and ring fingers proximate the PIP joints thereof.

15. The method of claim 14, wherein the step of securing the hand support section on the hand with straps comprises positioning an additional strap to extend through the slot formed in the hand support section, over the index, middle, and ring fingers, and around the radial side of the hand support section, whereby at least two straps extend through the slot.

16. The method of claim 15, wherein the additional strap extending around the radial side of the hand support section abuts the middle phalanx of each of the index, middle, and ring fingers.

17. The method of claim 15, wherein the step of securing the hand support section on the hand with a strap comprises positioning a strap to extend through the slot formed in the hand support section, over the little finger, and around the ulnar side of the hand support section, whereby at least three straps extend through the slot.

18. The method of claim 11, wherein the forearm support section comprises a thumb support section configured to abut the volar side of the thumb of the hand, and further comprising the step of securing the thumb support section to the thumb by positioning a strap to extend around the ulnar and radial sides of the thumb support section and over the thumb.

19. The method of claim 18, wherein the strap extending over the thumb further is received and retained within a side indentation located on the ulnar side of the thumb support section and within a side indentation located on the radial side of the thumb support section, and wherein the method further comprises the step of restraining flexion and adduction of the thumb relative to the thumb support section by bending a thumb restraint section that protrudes from a distal end of the thumb support section into blocking disposition of the thumb.

* * * * *